(12) United States Patent
Porro et al.

(10) Patent No.: US 12,387,823 B1
(45) Date of Patent: Aug. 12, 2025

(54) DEVICE AND METHOD FOR MEASURING A PLURALITY OF BLOOD PARAMETERS BY ARTIFICIAL INTELLIGENCE

(71) Applicant: DATAMED S.R.L., Peschiera Borromeo (IT)

(72) Inventors: Giampiero Porro, Dizzasco (IT); Alessandro Torinesi, Ornago (IT); Roberto Pozzi, Milan (IT); Giovanna Quarto, Vimodrone (IT); Luca Bolzoni, Milan (IT)

(73) Assignee: DATAMED S.R.L., Peschiera Borromeo (IT)

( * ) Notice: Subject to any disclaimer, the term of this patent is extended or adjusted under 35 U.S.C. 154(b) by 0 days.

(21) Appl. No.: 19/109,594

(22) PCT Filed: Oct. 26, 2023

(86) PCT No.: PCT/IB2023/060787
§ 371 (c)(1),
(2) Date: Mar. 7, 2025

(87) PCT Pub. No.: WO2024/089628
PCT Pub. Date: May 2, 2024

(30) Foreign Application Priority Data

Oct. 28, 2022 (IT) .................. 102022000022275

(51) Int. Cl.
*G16H 10/40* (2018.01)
*G01N 33/49* (2006.01)
(Continued)

(52) U.S. Cl.
CPC ............. *G16H 10/40* (2018.01); *G01N 33/49* (2013.01); *G16B 40/10* (2019.02)

(58) Field of Classification Search
CPC ........ G16B 40/10; G16B 40/20; G16B 40/30; G01N 33/49; G06N 3/02
See application file for complete search history.

(56) References Cited

U.S. PATENT DOCUMENTS 6,144,444 A * 11/2000 Haworth .............. A61B 5/1495
356/41
6,510,330 B1 * 1/2003 Enejder ................ G01N 21/532
356/39
(Continued)

FOREIGN PATENT DOCUMENTS

AU      2011222943 A1 *  8/2012 ............. A61B 5/157
WO  WO-2009120964 A2 * 10/2009 ........... A61B 5/0059
(Continued)

OTHER PUBLICATIONS

Matovic et al., "Predicting anemia using NIR spectrum of spent dialysis fluid in hemodialysis patients", May 18, 2021, Scientific Reports, vol. 11, pp. 1-15 (Year: 2021).*
(Continued)

*Primary Examiner* — Paulinho E Smith
(74) *Attorney, Agent, or Firm* — Manelli Selter PLLC; Edward Stemberger

(57) ABSTRACT

The present invention relates to a device (1, 1') and a method for simultaneously measuring a plurality of blood parameters by means of artificial intelligence. The invention provides for: exciting blood with electromagnetic radiation at a plurality of determined wavelengths, receiving analog information relating to the plurality of electromagnetic and/or light responses of the blood comprising electromagnetic radiation retroreflected or diffused by the blood, converting the analog electromagnetic and/or light response information into digital electromagnetic and/or light response data, processing the digital electromagnetic and/or light response data and the actual temperature value of the blood by means (Continued)

of one or more neural networks (NN) and determining, as a result of the processing operation, the value of each parameter.

23 Claims, 11 Drawing Sheets

(51) Int. Cl.
*G06N 3/02* (2006.01)
*G16B 40/10* (2019.01)

(56) References Cited

U.S. PATENT DOCUMENTS

| | | | | |
|---|---|---|---|---|
| 6,624,888 | B2* | 9/2003 | Panigrahi | G01N 33/025 |
| | | | | 356/326 |
| 10,948,478 | B2* | 3/2021 | Brun | G01N 27/026 |
| 11,226,282 | B2* | 1/2022 | Galavotti | A61B 5/14557 |
| 11,935,653 | B2* | 3/2024 | Hill, Jr. | G16H 50/20 |
| 2019/0226981 | A1* | 7/2019 | Galavotti | A61B 5/14557 |
| 2020/0141920 | A1* | 5/2020 | Glazier | G01N 33/6848 |
| 2021/0088502 | A1* | 3/2021 | Kjaer | G01N 33/49 |
| 2023/0301559 | A1* | 9/2023 | Kim | A61B 5/0095 |

FOREIGN PATENT DOCUMENTS

| | | | | |
|---|---|---|---|---|
| WO | 2022200875 | A1 | 9/2022 | |
| WO | WO-2022268997 | A1* | 12/2022 | G01N 21/31 |
| WO | WO-2024089628 | A1* | 5/2024 | A61B 5/14557 |

OTHER PUBLICATIONS

Liou et al., "Infrared Sensor Detection and Actuator Treatment Applied during Hemodialysis", Apr. 29, 2020, Sensors, vol. 20(9), pp. 1-17 (Year: 2020).*
Mathew et al., "Remote Blood Oxygen Estimation From Videos Using Neural Networks", Jul. 11, 2021, ArXiv.com, pp. 1-13 (Year: 2021).*
Decaro et al., "Machine Learning Approach for Prediction of Hematic Parameters in Hemodialysis Patients", Sep. 16, 2019, IEEE Journal of Translational Engineering in Health and Medicine, vol. 8, pp. 1-8 (Year: 2019).*
International Preliminary Report On Patentability in PCT/IB2023/060787 dated May 31, 2024.
International Search Report in PCT/IB2023/060787 dated Feb. 9, 2024.
Decaro et al., "Machine Learning Approach for Prediction of Hermatic Parameters in Hemodialysis Patients", IEEE Journal Of Translational Engineering In Health And Medicine, vol. 7, pp. 1-8, Oct. 4, 2029.

* cited by examiner

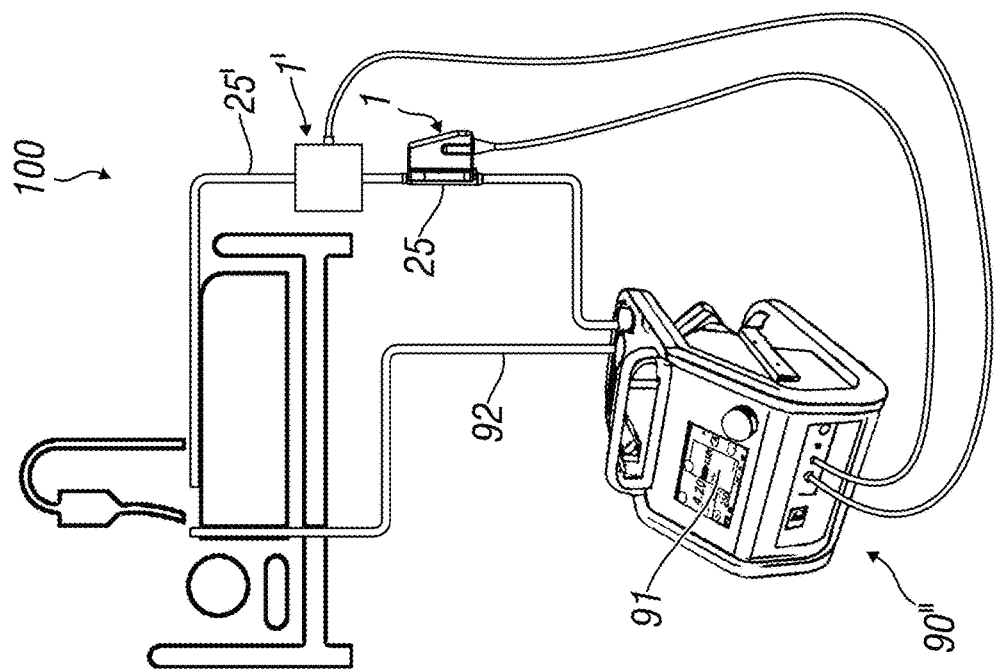
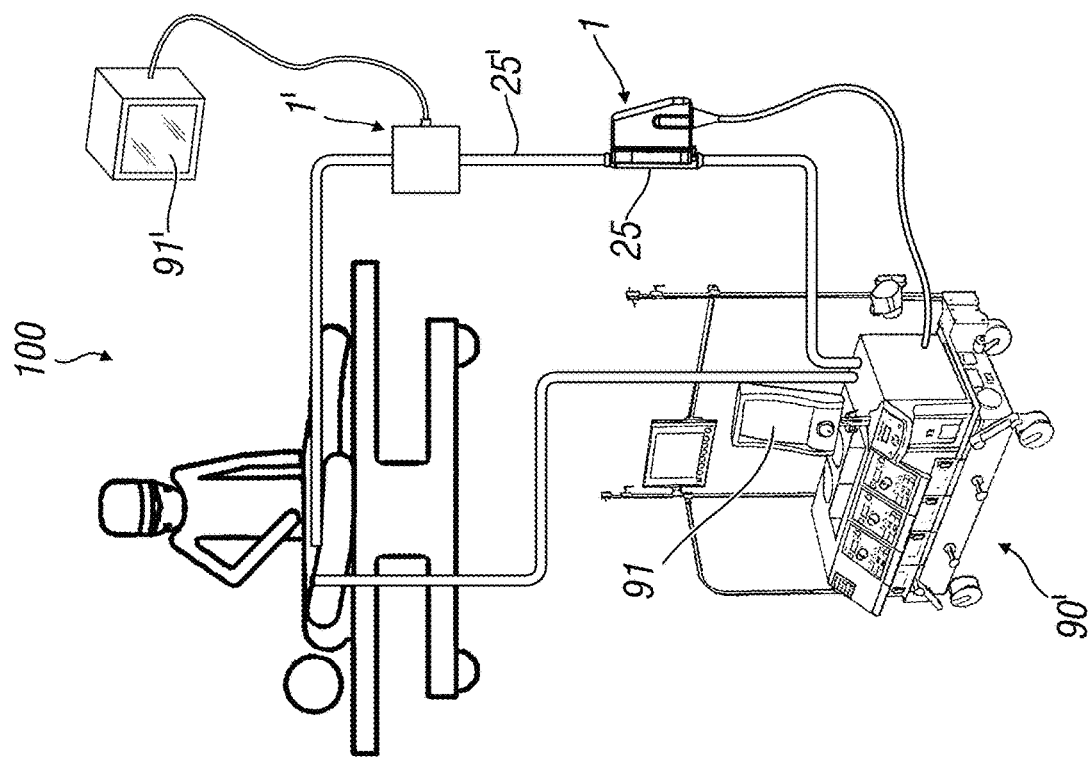
Fig. 8A
Fig. 8B $$z = b + \sum_{i=1}^{N} ai * wi$$

$$a_{out} = g(z)$$

DEVICE AND METHOD FOR MEASURING A PLURALITY OF BLOOD PARAMETERS BY ARTIFICIAL INTELLIGENCE

TECHNICAL FIELD OF THE INVENTION

The present invention relates to a device and method for measuring a plurality of blood parameters by artificial intelligence.

The device and method in accordance with the invention enable the measurement of the parameter in an extra-corporeal blood circuit.

The present invention also relates to a use of the device and an apparatus comprising the device.

The invention can be applied for monitoring blood parameters during therapies requiring extra-corporeal blood circulation such as haemodialysis, plasmapheresis, extra-corporeal respiratory assistance (ECMO), the preservation of explanted organs and cancer therapies.

PRIOR ART

Probes are known to measure a plurality of blood parameters in an extra-corporeal blood circuit.

A probe of this type is known from international patent application WO2010136962A1, which was filed in 2010 on behalf of the Applicant. Such a probe comprises a housing for containing a conduit for blood flowing in an extracorporeal circuit, emission means and means for detecting electromagnetic radiations, and a control unit to which the emission and detection means are connected. The control unit calculates the values of the blood parameters by means of a correlation between reference values and the ratios obtained from the light intensity values of the detected radiation; this correlation makes use of complex mathematical formulae.

The probe of WO2010136962A1 has some drawbacks; in particular, the complex mathematical formulas that are used cannot guarantee optimal accuracy in measuring the parameters. A further drawback is the inaccuracy of measurement when changing the blood conduit engaged to the probe with a blood conduit of a different formulation; this different conduit may have a hardness different from the previous conduit (more or less rigid conduit) and a different colour (due to chemical additives used in its manufacture) but the probe does not have the necessary accuracy to take into account these differences. The Applicant therefore noted that the measurement accuracy of the probe of WO2010136962A1 and the speed of measurement of the parameters could be improved and did so in accordance with the following.

AIMS OF THE INVENTION

The main purpose of the present invention is therefore to provide a device for measuring a plurality of blood parameters that is able to overcome the drawbacks described above in relation to the prior art.

The purpose of the present invention is to provide a device for measuring a plurality of blood parameters that does not require calibration by the end user prior to its use.

It is a further object of the invention to provide a method for measuring a plurality of blood parameters in such a way that the end user does not have to perform any calibration prior to measurement.

An additional aim of the invention is to propose a device and a method for measuring a plurality of blood parameters quickly, efficiently and reliably.

It is also an object of the invention to provide a device capable of measuring a plurality of blood parameters autonomously and with high accuracy over the entire measuring range of each parameter.

These and other purposes are achieved by a device, a use of the device, an apparatus and one or more methods in accordance with the following description, the attached claims and the following aspects.

SUMMARY OF THE INVENTION

Aspects of the invention are described herein. Where an aspect and/or claim recalls, by specific dependence on one or more other aspects or claims and/or by wording such as "the" or "said" and the like, one or more elements or steps or operations introduced by another aspect or claim, such aspect(s) and/or such claim(s) may be taken in combination therewith.

The invention provides a device (probe) for measuring a plurality of blood parameters equipped with a control unit that enables it to measure the parameters on the basis of a plurality of data of previous measurements of said parameters made during previous training.

The control unit implements the intelligence of the device and is responsible for carrying out the measurement autonomously. To make this possible, the control unit incorporates a coded calculation model (by means of program code) derived from a plurality of data from previous measurements of blood parameters made during previous training. In essence, the device learns from previous training and therefore, when in clinical use, is immediately ready for use without the need for prior calibration by the end user.

After a series of devices have undergone learning, the method is developed (the model and/or one or more algorithms, e.g. encoded in a firmware) that enables the subsequent devices produced to be used with a simple calibration performed in the laboratory, e.g. by the manufacturer of the device. All the end user has to do is using the device after connecting it to a tubular element (cuvette) or to a tube of an extra-corporeal blood circuit, without having to carry out any calibration.

Each device preferably has two types of information stored: a first type of information is common to the devices that are produced after said learning and relates to the 'calculation mechanisms' of the value of the parameters by the neural network (this type of information is preferably encoded in the device's firmware) and a second type of information that may vary for each device, e.g. due to hardware, variability of components and their specific geometric position within the device's box body (this type of information is preferably stored in a device memory).

Numbered aspects of the invention follow.

Device for Measuring a Plurality of Blood Parameters

1. Device for measuring a plurality of blood parameters by means of artificial intelligence including:
    at least one excitation member configured to excite blood, in particular a blood flow, with electromagnetic radiation at a plurality of determined wavelengths,
    at least one electromagnetic radiation detecting member, in particular at least one photodetector, configured to detect a plurality of electromagnetic responses, in particular light responses, of the blood comprising electromagnetic radiation, in particular light, being retro-reflected or diffused by blood, the electromagnetic radiation being retro-reflected or diffused by blood under operating conditions of the device following excitation by the excitation member.

2. Device for measuring a plurality of blood parameters by means of artificial intelligence including:
   at least one excitation member configured to excite a flow of blood at a plurality of determined wavelengths,
   at least one photodetector configured to detect a plurality of electromagnetic and/or light responses of the blood comprising light being retro-reflected or diffused by the blood under operating conditions of the device following excitation by the excitation member.

3. Aspect according to aspect 1 or 2, in which the device also includes a control unit configured to perform the following operations:
   commanding said at least one excitation member during an excitation step in which it excites blood with electromagnetic radiation at a plurality of determined wavelengths,
   receiving analogue information relating to the plurality of electromagnetic and/or light responses of the blood comprising electromagnetic radiation, in particular light, retro-reflected or diffused by the blood,
   converting the electromagnetic and/or light response analog information into electro-magnetic and/or light response digital data,
   processing said electromagnetic and/or light response digital data and the actual temperature value of blood by one or more neural networks,
   determining, as a result of the processing operation by one or more neural networks, the value of each parameter of the plurality of blood parameters.

4. Aspect according to aspect 3, the control unit being configured to process said electromagnetic and/or light response digital data and the actual temperature value of blood by one or more neural networks and determine the value of each parameter of said plurality of blood parameters by means of the following operations:
   determining a plurality of ratios, each ratio being defined between a magnitude indicative of the radiation retro-reflected or diffused by the blood due to an excitation at a determined wavelength and a magnitude indicative of the radiation retro-reflected or diffused by the blood due to an excitation at another determined wavelength,
   providing as input to one or more neural networks said plurality of ratios and the temperature value,
   processing said plurality of ratios by means of one or more neural networks taking into account a plurality of data of previous measurements of said blood parameters made during previous training,
   providing as an output from one or more neural networks the value of each parameter of the plurality of blood parameters.

5. Aspect according to any of the preceding aspects, in which the device includes a temperature sensor configured to measure the actual temperature of the blood.

6. Aspect according to any one of the preceding aspects, in which the device is configured to simultaneously measure a plurality of blood parameters by artificial intelligence.

7. Aspect according to any one of the preceding aspects, wherein the control unit is configured to detect the value of each parameter of said plurality of blood parameters which the artificial intelligence deems corresponding, on the basis of said plurality of data from previous measurements, to previously determined ratios.

8. Aspect according to any one of the preceding aspects, in which the device comprises a firmware and the control unit comprises artificial intelligence information, e.g. one or more matrices usable by said one or more neural networks, encoded in the firmware and enabling the calculation of said plurality of parameters by one or more neural networks. This information encoded in a firmware is 'the same for all devices'.

9. Aspect according to any one of the preceding aspects, wherein the device comprises a memory, the control unit being configured to provide as input to the one or more neural networks a reference value of a first parameter to be measured and a reference value of a second parameter to be measured, said reference values being acquired and stored in the memory of the device, preferably during a calibration step prior to use of the device, said memory thereby comprising information relating to said reference values.

10. Aspect according to any of the preceding aspects, in which the device comprises a memory comprising one or more pieces of information, e.g. one or more matrices usable by said one or more neural networks, uniquely associated with a calibration step of the device.

11. Aspect according to any one of the preceding aspects, where the device calibration step is carried out by the manufacturer of the device.

12. Aspect according to any one of the preceding aspects, where the calibration step is not performed by the end user of the device 13. Aspect according to any one of the preceding aspects, where the calibration step is not carried out during or just prior to the conditions of use of the device.

This information and/or reference parameters stored in the memory of the device are specific to each device being manufactured and take into account variability between devices (variability due to e.g. hardware, variability of components and their even infinitesimal geometric position within the device's box body) and to give a firm starting point for the measurement of oxygen saturation and hematocrit expected under calibration conditions.

14. Aspect according to any one of the preceding aspects, where the control unit comprises a microprocessor, this information being encoded in the microprocessor's firmware.

15. Aspect according to any one of the preceding aspects, in which the device is configured to measure, by means of artificial intelligence, oxygen saturation, i.e. $SatO_2$, hematocrit, i.e. Hct, and optionally to also measure hemoglobin content, i.e. Hb.

16. Aspect according to any one of the preceding aspects, wherein the control unit is configured to control said at least one excitation member or both excitation members during an excitation step which involves exciting the blood flow one wavelength at a time.

17. Aspect according to any one of the preceding aspects, wherein the device comprises a plurality of excitation members and the control unit is configured to control the plurality of excitation members during an excitation step to activate the plurality of excitation members in accordance with a determined time sequence.

18. Aspect according to any of the preceding aspects, wherein said at least one excitation member is configured to excite a flow of blood at least at the following wavelengths: 660 nm, 805 nm, 1450 nm and at least one between 525 nm, 940 nm and 1050 nm.

19. Aspect according to any one of the preceding aspects, wherein said at least one excitation member is configured to excite a flow of blood at at least the following wavelengths: 660 nm, 805 nm, 1450 nm and at least two between 525 nm, 940 nm and 1050 nm.

20. Aspect according to any of the preceding aspects, in which said at least one excitation member is configured to excite a flow of blood at least at the following wavelengths: 660 nm, 805 nm, 1450 nm, 525 nm, 940 nm and 1050 nm.

21. Aspect according to any one of the preceding aspects, wherein the device comprises a first excitation member configured to excite blood flow at least at a first wavelength, in particular at a first plurality of wavelengths, and a second excitation member configured to excite blood flow at least at a second wavelength, in particular at a second plurality of wavelengths.

22. Aspect according to aspect 21, wherein the control unit is configured to activate, preferably alternately, the first excitation member and the second excitation member so as to excite, preferably alternately, the blood flow at the first wavelength or first plurality of wavelengths and at the second wavelength or second plurality of wavelengths.

23. Aspect according to any of the preceding aspects, in which the device comprises a first excitation member and a second excitation member.

24. Aspect according to aspect 23, in which the first and second excitation members are configured to excite the blood at a respective plurality of different wavelengths.

25. Aspect according to aspect 23 or 24, in which the first excitation member is configured to excite blood flow at the following wavelengths: 525 nm, 940 nm, optionally 1050 nm.

26. Aspect according to aspect 23 or 24 or 25, in which the second excitation member is configured to excite the blood flow at the following wavelengths: 660 nm, 805 nm, 1450 nm.

27. Aspect according to any one of the preceding aspects, wherein each excitation member comprises a plurality of LED elements configured to emit light radiation at said wavelengths, in particular a plurality of LED elements equal in number to said wavelengths in which each LED is configured to operate.

28. Aspect according to any one of aspects 23 to 27, in which the first excitation member and the second excitation member are arranged within the box body.

29. Aspect according to any one of aspects 23 to 28, in which the first excitation member and the second excitation member are arranged side by side.

30. Aspect according to any one of the preceding aspects, wherein the device comprises a first electromagnetic radiation detecting member and a second electromagnetic radiation detecting member, each electromagnetic radiation detecting member being configured to detect a plurality of electromagnetic and/or light responses of the blood, in particular to detect a plurality of electromagnetic and/or light responses of the blood respectively at different pluralities of wavelengths.

31. Aspect according to any one of the preceding aspects, wherein the device comprises a first photodetector and a second photodetector, each photodetector being configured to detect a plurality of electromagnetic and/or light responses of the blood, in particular to detect a plurality of electromagnetic and/or light responses of the blood at different pluralities of wavelengths, respectively.

32. Aspect according to aspect 31, in which the first photodetector and the second photodetector are arranged within the box body.

33. Aspect according to aspect 31 or 32, in which the first photodetector and the second photodetector are arranged side by side.

34. Aspect according to aspect 31 or 32 or 33, in which the first and second photodetectors are configured to detect the blood response at a respective plurality of different wavelengths.

35. Aspect according to any one of aspects 31 to 34, wherein the first photodetector is configured to detect the light response of the blood upon excitation at the following wavelengths: 660 nm, 805 nm, 525 nm, 1050 nm, 940 nm.

36. Aspect according to any one of aspects 31 to 35, in which the second photodetector is configured to detect the light response of the blood upon excitation at the following wavelengths: 805 nm and 1450 nm.

37. Aspect according to any one of the preceding aspects, wherein the device comprises a box body, said at least one or each excitation member, said at least one or each electromagnetic radiation detecting member and said control unit being housed within the box body.

37-bis. Aspect according to any one of the preceding aspects, wherein the device, particularly the box body, comprises a coupling portion configured to allow coupling of the device with the container.

37-tris. Aspect according to aspect 37 and 37-bis, in which the coupling portion is joined to or engaged with the box body and/or is integral with the box body.

37-quater. Aspect according to 37-bis or 37-tris, wherein the coupling portion is configured to allow coupling of the box body to the container.

37-quinquies. Aspect according to any of the preceding aspects, wherein the device, in particular the box body, is substantially pocket-sized.

37-sexies. Aspect according to any of the preceding aspects, where the device, in particular the box body, has one or more characteristic dimensions (such as width, height and length) of less than 100 mm, preferably each characteristic dimension being less than 100 mm.

37-sexies. Aspect according to any of the preceding aspects, wherein the device does not include a screen.

Flow Information

38. Aspect according to any of the previous aspects, in which the control unit is configured to take into account a value related to blood flow, in particular the volumetric flow rate of blood, when measuring oxygen saturation and/or hematocrit.

39. Aspect according to any one of the preceding aspects, in which the control unit is configured to perform the operation of taking into account a blood flow-dependent value in the measurement of oxygen saturation and/or hematocrit by correcting the measured values of oxygen saturation and/or hematocrit to blood flow.

40. Aspect according to any of the preceding aspects, in which the control unit is configured to make available, preferably at the same instant, the value of each parameter of said plurality of blood parameters.

Embodiment for Cuvette

41. Aspect according to any one of the preceding aspects, wherein the device comprises a coupling portion joined to the box body and comprising at least one coupling element, the coupling portion being configured to present:
- a coupled configuration in which it is coupled to a container by means of said at least one coupling element, the container being capable of containing blood and/or configured to allow a flow of blood therein,
- a decoupled configuration in which it is not coupled to the container.

42. Aspect according to aspect 41, in which said at least one coupling element is magnetic and is configured to allow magnetic coupling with the container.

43. Aspect according to any one of the preceding aspects, wherein the device comprises a first and a second coupling element arranged at opposing longitudinal portions of the device and configured to couple with corresponding magnetic elements located at respective longitudinal portions or ends of the container.

44. Aspect according to any of the previous aspects, in which each coupling element is magnetic and is configured to allow magnetic coupling with the container.

Embodiment for Tube

45. Aspect according to any of the preceding aspects, in which the device is associated with a container, e.g. a tube, into which blood may flow, under operating conditions the device being associated with said container.

46. Aspect according to any of the previous aspects, in which the control unit is configured to perform the following operations:
    detecting a type of container, in particular a type of tube,
    preparing for measurement on the basis of the type of container, in particular of the type of tube, detected.

47. Aspect according to aspect 46, wherein the control unit is configured to prepare for measurement based on the type of container or tube detected by the operation of adapting the measurement mode of one or more parameters to the type of container or tube detected.

48. Aspect according to aspect 46 or 47, wherein the control unit is configured to detect a type of container or tube and prepare for measurement based on the type of container or tube detected prior to the operation of exciting a flow of blood at a plurality of determined wavelengths.

49. Aspect according to aspect 46 or 47 or 48, in which the control unit is configured to detect the colour of the container, in particular the colour of the tube.

50. Aspect according to any one of aspects 46 to 49, wherein the control unit is configured to perform the operation of preparing for measurement on the basis of the type or colour of container or tube detected by selection of a determined matrix from a plurality of matrices usable by the neural network.

51. Aspect according to aspect 50, wherein the control unit is configured to select a determined matrix from a plurality of matrices usable by the neural network by consulting a memory in which information relating to said plurality of matrices is stored.

52. Aspect according to any one of the preceding aspects, wherein the device comprises a box body, a covering element movable with respect to the box body and a seat suitable for holding a container, in particular a portion of a tube of an extra-corporeal blood circuit, into which blood flows under operating conditions of the device, the covering element being configured to operate at least between the following configurations:
    an operative configuration in which it flattens opposite surfaces of the container housed at the seat,
    a rest configuration.

53. Aspect according to aspect 52, in which the covering element is movable by rotation relative to the box body.

54. Aspect according to aspect 52 or 53, the covering element comprising a compression element for compressing, in the operative configuration of the covering element, the container housed at the seat.

55. Aspect according to aspect 54, in which the compression element is configured to determine a reduction in the fluid passage cross-section of the container of between 9% and 17%.

56. Aspect according to aspect 55, in which the reduction of the fluid passage cross-section occurs for a length between 15 and 30 mm or equal to one of these values.

57. Aspect according to any one of aspects 52 to 56, wherein the compression element comprises opposing curved ends and a flat portion defined between said ends, the flat portion being configured to determine a flat reading area at a surface of the container, in particular at an upper surface of the container and/or at a lower surface of the container.

58. Aspect according to any one of aspects 52 to 57, wherein the device comprises at least one constraining element configured to maintain the covering element in the operative configuration.

59. Aspect according to any one of aspects 52 to 58, wherein the device comprises two constraining elements configured to maintain the covering element in the operative configuration, the two constraining elements being opposed to each other.

60. Aspect according to any one of aspects 52 to 59, wherein the covering element is hinged to the box body at a hinging portion, said at least one constraining element being opposed to the hinging portion.

61. Aspect according to any one of aspects 52 to 60, wherein the device comprises a sensor configured to verify the configuration (preferably the position) of the covering element, in particular to verify that the covering element is in the operative configuration (preferably in the closed position), and the control unit is configured to obtain information regarding the configuration (preferably the position) assumed by the covering element via the sensor.

62. Aspect according to any one of aspects 52 to 61, in which the control unit is configured to prevent measurement of parameters when the covering element is in the rest configuration (preferably in the open position).

63. Aspect according to any one of aspects 52 to 62, in which the control unit is configured to allow measurement of parameters only when the covering element is in the operating configuration (preferably in the closed position).

64. Aspect according to any one of aspects 52 to 63, wherein the covering element comprises a body and a compression element configured to oscillate with respect to said body.

65. Aspect according to aspect 64, in which the compression element is tilting relative to the body.

66. Aspect according to any one of aspects 54 to 65, in which the covering element drags the compression element in rotation.

67. Aspect according to aspect 64 or 65 or 66, in which the compression element is configured to describe an angle different from an angle described by the body of the covering element.

68. Aspect according to any one of aspects 64 to 67, wherein the compression element is configured to rotate by a different angle than a rotation angle of the covering element body.

69. Aspect according to any one of aspects 64 to 68, wherein the covering element comprises a pin operatively arranged between the body and the compression element, the compression element being configured to swing relative to the body by means of said pin.

Use

70. Use of the device, in accordance with any of the appended device claims and/or any of the preceding device aspects, for measuring, in particular measuring simultaneously, a plurality of blood parameters.

71. Aspect according to aspect 70, in which the simultaneous measurement of said plurality of blood parameters is carried out by means of artificial intelligence.

72. Aspect according to aspect 70 or 71, in which use is made in an extra-corporeal blood circuit.

73. Aspect according to aspect 70 or 71 or 72, in which use does not involve any initial calibration of the device by the end user.

74. Aspect according to any one of aspects 70 to 73, wherein the use provides for the measurement of a plurality of parameters by artificial intelligence, in particular by one or more neural networks.

75. Aspect according to any one of aspects 70 to 74, wherein the use provides for measuring said plurality of blood parameters flowing within a cuvette connected to an extra-corporeal blood circuit.

76. Aspect according to any one of aspects 70 to 75, wherein the use provides for the measurement of said plurality of blood parameters at a portion of a tube of an extra-corporeal blood circuit.

Assembly

77. Assembly comprising:
    a device in accordance with any of the attached device claims and/or the preceding device aspects,
    a container capable of containing blood and/or configured to allow a flow of blood therein, preferably the container being a cuvette or a tube or tube piece of an extra-corporeal blood circuit.

Apparatus

78. Apparatus comprising:
    a device in accordance with any of the attached device claims and/or the preceding device aspects,
    a medical machine, e.g. a heart-lung machine or an extracorporeal membrane oxygenation machine,
    a user interface, such as a display means, operatively connected or connectable to the device and configured to make available the measured values of said plurality of blood parameters.

Method for Measuring a Plurality of Blood Parameters

79. A method for measuring a plurality of blood parameters by artificial intelligence, the method comprising the following steps:
    exciting blood, in particular a blood flow, with electromagnetic radiation at a plurality of determined wavelengths,
    detecting a plurality of electromagnetic responses, in particular light responses, of the blood comprising electromagnetic radiation, in particular light, retro-reflected or diffused by the blood,
    receiving analogue information regarding the plurality of electromagnetic and/or light responses of blood comprising light retro-reflected or diffused by blood,
    converting the electromagnetic and/or light response analog information into electro-magnetic and/or light response digital data,
    processing said electromagnetic and/or light response digital data and the actual temperature value of blood by one or more neural networks,
    determining, as a result of the processing operation by one or more neural networks, the value of each parameter of the plurality of blood parameters.

80. A method for measuring a plurality of blood parameters by artificial intelligence, the method comprising the following steps:
    exciting a flow of blood at a plurality of determined wavelengths,
    detecting a plurality of electromagnetic and/or light responses of the blood including light retro-reflected or diffused by blood,
    receiving analogue information about the plurality of electromagnetic and/or light responses of the blood including light retro-reflected or diffused by blood,
    converting analogue light response information into light response digital data,
    processing said light response digital data and the actual blood temperature value by one or more neural networks,
    determining, as a result of the processing operation by one or more neural networks, the value of each parameter of the plurality of blood parameters.

81. Aspect according to aspect 79 or 80, wherein the steps of processing said electromagnetic and/or light response digital data and the actual temperature value of blood by one or more neural networks and determining the value of each parameter of said plurality of blood parameters comprise:
    determining a plurality of ratios, each ratio being defined between a magnitude indicative of the radiation retro-reflected or diffused by the blood due to an excitation at a determined wavelength and a magnitude indicative of the radiation retro-reflected or diffused by the blood due to an excitation at another determined wavelength,
    providing as input to one or more neural networks said plurality of ratios,
    processing said plurality of ratios by means of one or more neural networks taking into account a plurality of data of previous measurements of said blood parameters made during previous training,
    providing as an output from one or more neural networks the value of each parameter of the plurality of blood parameters.

82. Aspect according to aspect 79 or 80 or 81, the method comprising arranging a device in accordance with any one of the appended device claims and/or the preceding device aspects and is carried out by means of said device.

83. Aspect according to any one of aspects 79 to 82, wherein the method is carried out by means of a device according to any one of the appended device claims and/or the preceding device aspects.

84. Aspect according to any one of aspects 79 to 83, wherein the method comprises detecting the actual temperature value of the blood, preferably by means of a temperature sensor housed within the box body of the device.

85. Aspect according to any one of aspects 79 to 84, wherein the method is a method for simultaneously measuring a plurality of blood parameters by means of artificial intelligence.

86. Aspect according to any one of aspects 79 to 85, wherein the method comprises the step of simultaneously making available measured values of said plurality of blood parameters.

87. Aspect according to any one of aspects 79 to 86, wherein the step of processing said plurality of ratios by means of the one or more neural networks taking into account a plurality of data from previous measurements of said blood parameters made during previous training comprises detecting the value of each parameter of said plurality of blood parameters that the artificial intelligence deems corresponding, on the basis of said plurality of data from previous measurements, to the previously determined ratios.

88. Aspect according to any one of aspects 79 to 87, wherein the method further comprises providing as input to the one or more neural networks a reference value of a first parameter to be measured and a reference value of a second parameter to be measured, said reference values being acquired and stored in the device during a calibration step prior to use of the device.

89. Aspect according to aspect 87 or 88, wherein the step of detecting the value of each parameter of said plurality of blood parameters that the artificial intelligence deems corresponding, based on said plurality of data from previous measurements, to the previously determined ratios comprises processing data and/or information by means of a mathematical matrix model, preferably by means of one or more matrices of weights and biases.

90. Aspect according to any one of aspects 79 to 89, wherein the step of exciting a blood flow at a plurality of determined wavelengths comprises activating a plurality of excitation members in accordance with a determined time sequence.

91. Aspect according to aspect 90, in which the step of activating a plurality of excitation members in accordance with a determined time sequence includes alternately activating a first excitation member and a second excitation member.

92. Aspect according to any one of aspects 79 to 91, wherein the step of detecting a plurality of blood electromagnetic responses comprises:
   detect a plurality of electromagnetic and/or light responses of the blood by means of an initial photodetector,
   detect a plurality of electromagnetic and/or light responses of the blood by means of a second photodetector.

93. Aspect according to any one of aspects 79 to 92, wherein blood excitation is carried out under device operating conditions in which a flow of blood flows into a container associated with the device.

94. Aspect according to any one of aspects 79 to 93, wherein the container associated with the device is a cuvette, in particular associated with, or arranged in, an extra-corporeal blood circuit.

95. Aspect according to any one of aspects 79 to 94, wherein the container associated with the device is a tube or a tube portion of an extra-corporeal blood circuit.

96. Aspect according to any one of aspects 79 to 95, wherein the method comprises the step of making available, preferably at the same instant, the value of each parameter of said plurality of blood parameters on a medium that can be consulted by an operator, for example on a screen of a machine associated with the device configured to carry out said method for measuring a plurality of blood parameters by artificial intelligence.

Flow Information

97. Aspect according to any one of aspects 79 to 96, wherein the method comprises the step of taking into account a value related to blood flow, in particular the volumetric flow rate of blood, when measuring oxygen saturation and/or hematocrit.

98. Aspect according to any one of aspects 79 to 97, wherein the step of taking into account a value related to blood flow in the measurement of oxygen saturation and/or hematocrit includes correcting the measured values of oxygen saturation and/or hematocrit depending on blood flow.

Detection of Type (Colour) of Container

99. Aspect according to any of aspects 79 to 98, where the method also includes the steps of:
   detecting a type of container, in particular a type of tube,
   adapting the mode of measurement of one or more parameters to the type of tube detected, preferably wherein the step of detecting a container type, particularly a tube type, includes detecting the colour of the container, particularly the colour of the tube.

100. Aspect according to aspect 99, wherein the method comprises the step of preparing the control unit of the device for measurement based on the type of tube detected, said step comprising the step of adapting the mode of measurement of one or more parameters to the type of tube detected.

101. Aspect according to aspect 99 or 100, in which the step of detecting a container type, particularly a tube type, is carried out while a saline solution or other fluid other than blood is flowing in the container.

102. Aspect according to aspect 99 or 100 or 101, wherein the step of detecting a container type, in particular a tube type, is carried out prior to the step of exciting a blood flow at a plurality of determined wavelengths.

103. Aspect according to any one of aspects 99 to 102, wherein the step of adapting the mode of measurement of one or more parameters to the type of tube detected comprises the step of selecting a determined matrix from a plurality of matrices usable by the neural network.

104. Aspect according to aspect 103, wherein the step of selecting a determined matrix from a plurality of matrices usable by the neural network includes consulting a memory in which information relating to said plurality of matrices is stored.

105. Aspect according to aspect 104, where memory is the memory of the device configured to implement the method.

Engagement Between Device and Container

106. Aspect according to any one of aspects 79 to 105, wherein the method comprises the step of associating the device to a container, for example to a tubular element such as a cuvette or to a tube such as a tube of an extra-corporeal blood circuit.

107. Aspect according to aspect 106, in which the step of associating the device with a container includes constraining the device and container relatively.

108. Aspect according to aspect 107, in which the step of constraining relatively device and container comprises:
   magnetically constraining device and container, e.g. by means of one or more magnetic coupling elements, and/or
   mechanically constraining device and container, e.g. by means of at least one mechanical constraining element.

109. Aspect according to aspect 108, wherein the step of mechanically constraining the device and container comprises engaging a covering element with respect to a box body of the device by means of at least one constraining element, in particular by means of two constraining elements opposed to each other.

110. Aspect according to aspect 108 or 109, wherein the step of mechanically constraining device and container comprises moving, in particular rotating, a covering element in approach with respect to a box body of the device.

111. Aspect according to any one of aspects 79 to 110, wherein the method comprises flattening opposing surfaces of the container associated with the device, said step being carried out prior to exciting a flow of blood at a plurality of determined wavelengths.

112. Aspect according to aspect 111, in which the flattening step of the opposing surfaces of the container associated with the device comprises compressing a tube of an extra-corporeal blood circuit.

113. Aspect according to aspect 111 or 112, in which the step of flattening opposing surfaces of the container associated with the device is carried out after the step of associating the device with a container.

114. Aspect according to any one of aspects 79 to 113, wherein the method further comprises the step of compressing a portion of a container within which blood flows or may flow.

115. Aspect according to aspect 114, in which the step of compressing a portion of a container determines a reduction of the fluid passage cross-section of the container of between 9% and 17%.

116. Aspect according to aspect 115, in which the reduction of the fluid passage section occurs for a length between 15 and 30 mm or equal to one of these values.

117. Aspect according to aspect 114 or 115 or 116, wherein the step of compressing a portion of a container within which blood flows or may flow is performed prior to the step of determining as a result of the processing operation by the one or more neural networks, the value of each parameter of said plurality of blood parameters, in particular prior to the step of exciting blood.

118. Aspect according to any one of aspects 79 to 117, wherein the method comprises the step of swinging a compression element relative to a container within which blood flows or may flow.

119. Aspect according to aspect 118, in which the step of swinging a compression element relative to a container is realised during a step of moving, in particular rotating, an approaching covering element relative to a box body of the device.

120. Aspect according to aspect 118 or 119, in which the step of swinging a compression element relative to a container is realized by swinging a tilting compression element.

121. Aspect according to aspect 118 or 119 or 120, in which the step of swinging a compression element involves progressively and/or gently compressing the container.

Other Aspects

122. Aspect according to any of the previous aspects, where each ratio is a ratio of optical counts taken at respective wavelengths.

123. Aspect according to any one of the preceding aspects, wherein the one or more neural networks takes/take into account a plurality of data of previous measurements of said blood parameters made during previous training by means of at least one matrix, in particular at least one matrix of weights and biases.

124. Aspect according to any one of the preceding aspects, wherein the container in which the blood flows is of disposable type.

125. Aspect according to any one of the preceding aspects, wherein the device is configured to measure at least two blood parameters by artificial intelligence.

126. Aspect according to aspect 125, in which said at least two blood parameters are the oxygen saturation of the blood and the hematocrit value of the blood.

127. Aspect according to any one of the preceding aspects, where the device is configured to measure at least three blood parameters.

128. Aspect according to aspect 125 or 126 or 127, wherein the device is configured to measure said at least two blood parameters directly by artificial intelligence and to measure a third blood parameter as a parameter derived from the measurement of at least one of said two parameters.

129. Aspect according to aspect 127 or 128, where the third parameter is hemoglobin content or concentration.

130. Aspect according to any one of the preceding aspects, in which the device is configured to measure four blood parameters.

131. Aspect according to aspect 130, in which said four blood parameters are: blood oxygen saturation, blood hematocrit value, hemoglobin content or concentration and blood temperature.

132. Aspect according to any one of the preceding aspects, wherein the device is configured to be associated with a cuvette and has no relative rotating parts to allow engagement between cuvette and device.

133. Aspect according to any one of aspects 31 to 132, in which the first photodetector comprises a silicon photodiode (or Si photodiode).

134. Aspect according to any one of aspects 31 to 133, wherein the second photodetector comprises an indium, gallium and arsenic photodiode (or InGaAs photodiode).

135. Aspect according to any one of the preceding aspects, in which the artificial intelligence can measure (directly or indirectly) the following parameters: blood oxygen saturation ($SatO_2$), hematocrit (Hct) and hemoglobin (Hb).

136. Aspect according to any one of the preceding aspects, wherein the measurement of the plurality of parameters takes place in the following manner:
 direct measurement of blood oxygen saturation in percentage value, i.e. $SatO_2$ [%],
 direct measurement of the blood hematocrit value, i.e. Hct [%],
 direct measurement of blood temperature, i.e. Temp. [° C.],
 indirect (derived) measurement of hemoglobin content in blood, i.e. its concentration, Hb [g/dl].

137. Aspect according to any one of the preceding aspects, wherein the measurement of the plurality of parameters takes place in the following manner:
 direct measurement by artificial intelligence of blood oxygen saturation in percentage value, i.e. $SatO_2$ [%],
 direct measurement by artificial intelligence of the blood hematocrit value, i.e. Hct [%],
 direct measurement using a temperature sensor of blood temperature, i.e. Temp. [° C.],
 measurement indirectly by artificial intelligence of the hemoglobin content of the blood, that is its concentration, i.e. Hb [g/dl].

138. Aspect according to any of the previous aspects, in which the measurement of parameters is carried out by means of the same measurement operation or session.

139. Aspect according to any of the previous aspects, in which the calculation model implemented by one or more neural networks is a mathematical matrix model.

Machine Learning Method

140. A machine learning method based on one or more neural networks comprising the following steps:
 providing a machine-learning set-up, this step comprising coupling a plurality of devices to corresponding containers arranged along, and/or part of, an extracorporeal blood circuit,
 performing one or more training epochs in which the desired blood parameters (hematocrit, oxygen saturation, temperature and, optionally, hemoglobin) are measured while blood flows through the containers,
 developing a calculation method configured to allow the calculation, by means of artificial intelligence, of one or more of said parameters.

141. Aspect according to aspect 140, wherein the machine learning method may comprise steps 1) to 7) set forth in the corresponding section of the following detailed description.

142. Aspect according to aspect 140 or 141, wherein the machine learning method is implemented as per the machine learning set-up in accordance with the corresponding section of the following detailed description.

Conventions and Definitions

Note that in the following detailed description corresponding parts/components/elements are indicated with the same numerical references. The figures may illustrate the subject matter of the invention by means of non-scaled representations; therefore, parts/components/elements illustrated in the accompanying figures and relating to the subject matter of the invention may relate only to schematic representations. In the context of the present disclosure, the use of terms such as "above", "upper", "at the top", "below", "lower", "at the bottom", "sideways", "lateral", "laterally", "inside", "internally", "outside", "externally", "horizontal", "horizontally", "vertical", "vertically", "frontal", "frontally", "rear", "rearward", "right", "left", similar terms and variations thereof refer, unless otherwise specifically indicated, to at least one spatial orientation that the object of the invention may assume under conditions of use (see, for example, one or more of the appended figures). Unless otherwise specifically indicated, the terms 'condition' or 'configuration' may be used interchangeably in the context of the present disclosure. Unless otherwise specifically indicated, expressions such as "upstream", "downstream" and similar or derivative expressions refer to the arrangement of parts/components/elements with respect to the direction of fluid flow along a fluid line or circuit or to a determined line or branch of the circuit in which said elements are displaced.

In the context of the present disclosure, one or more of the following definitions/conventions are applicable where appropriate and except where otherwise indicated and/or except where the context excludes this (e.g. for technical reasons):

the device is configured to measure the following plurality of parameters: oxygen saturation (i.e. $SatO_2$), hematocrit (i.e. Hct), blood temperature and optionally also hemoglobin content (i.e. Hb);

the device is preferably a probe;

the device is preferably configured to measure simultaneously said plurality of parameters;

'measuring simultaneously' means 'measuring by means of the same measurement operation or session', in particular it means 'measuring by means of the same measurement operation or session a plurality of blood parameters by making available simultaneously the measured values of said plurality of blood parameters';

the device is configured to measure:

oxygen saturation of the blood in percentage value, i.e. $SatO_2$ [%], blood hematocrit value, i.e. Hct [%], blood temperature, i.e. Temp. [° C.], optionally, hemoglobin content in the blood or its concentration, i.e. Hb [g/dl], of which the oxygen saturation of the blood, the hematocrit value of the blood, and where applicable, the hemoglobin content of the blood or its concentration, are measured by artificial intelligence, while the temperature of the blood is measured using a temperature sensor;

the plurality of blood parameters measured by artificial intelligence may comprise 'at least two blood parameters' (i.e. $SatO_2$, Hct), more specifically 'three blood parameters' (i.e. $SatO_2$, Hct, and Hb), even more specifically 'exclusively three blood parameters' (i.e. exclusively $SatO_2$, Hct, and Hb);

the device is configured to measure multiple parameters in the following way:

direct measurement by artificial intelligence of blood oxygen saturation in percentage value, i.e. $SatO_2$ [%], direct measurement by artificial intelligence of the blood hematocrit value, i.e. Hct [%], direct measurement of blood temperature, i.e. Temp. [° C.], preferably using a temperature sensor, indirect measurement (derived from a direct measurement by artificial intelligence) of the hemoglobin content of blood, i.e. its concentration, Hb [g/dl]; note how the hemoglobin content is a parameter derived from the direct measurement of the blood hematocrit value;

with regard to the direct measurements, the device is configured to measure parameters in the respective ranges with high accuracy, i.e:

13-55% for blood hematocrit, 35-99.9% for blood oxygen saturation, 9-42° C. for blood temperature.

'retro-reflected electromagnetic radiation' or 'retro-reflected light' means electromagnetic radiation or light that returns back to the photodetector, following excitation of the blood, after having passed through the medium (blood) and thus having been partly absorbed. It corresponds to the optical counts read by the photodetector (photodiode). 'Electromagnetic radiation' can also be referred to simply as 'radiation';

'light' refers to radiation in the visible part of the electromagnetic spectrum;

each 'optical count' is a measurement indicative of the signal (electromagnetic radiation) detected by the photodetector (photodiode) following excitation by electromagnetic radiation at a determined wavelength; optical counts are used to determine or calculate ratios and are referred to as 'counts' in FIG. 12.

The aforesaid conventions and definitions may be used, where necessary, to interpret the claims. If necessary, one or more of said conventions and definitions may be included in one or more of the following claims and/or in one or more of the preceding aspects, in particular when said claims and/or aspects use one or more expressions covered by one or more conventions or definitions.

BRIEF DESCRIPTION OF THE DRAWINGS

In order to better understand the invention and appreciate its advantages, some embodiments are described below, by way of example and not limitation, with reference to the attached figures, in which:

FIG. 8A illustrates a possible clinical use of both the device of FIG. 1 (shown top right in the extracorporeal blood circuit) and the device of FIG. 4 (shown bottom right in the extra-corporeal blood circuit) in an operating theater, where the device can be used in cooperation with a heart-lung machine;

FIG. 8B illustrates another possible clinical use of both the device of FIG. 1 (shown top right in the extracorporeal blood circuit) and the device of FIG. 4 (shown bottom right in the extracorporeal blood circuit) in intensive care, wherein the device can be used in cooperation with an extracorporeal membrane oxygenation machine (ECMO);

DETAILED DESCRIPTION OF EMBODIMENTS OF THE INVENTION

Figure 1:
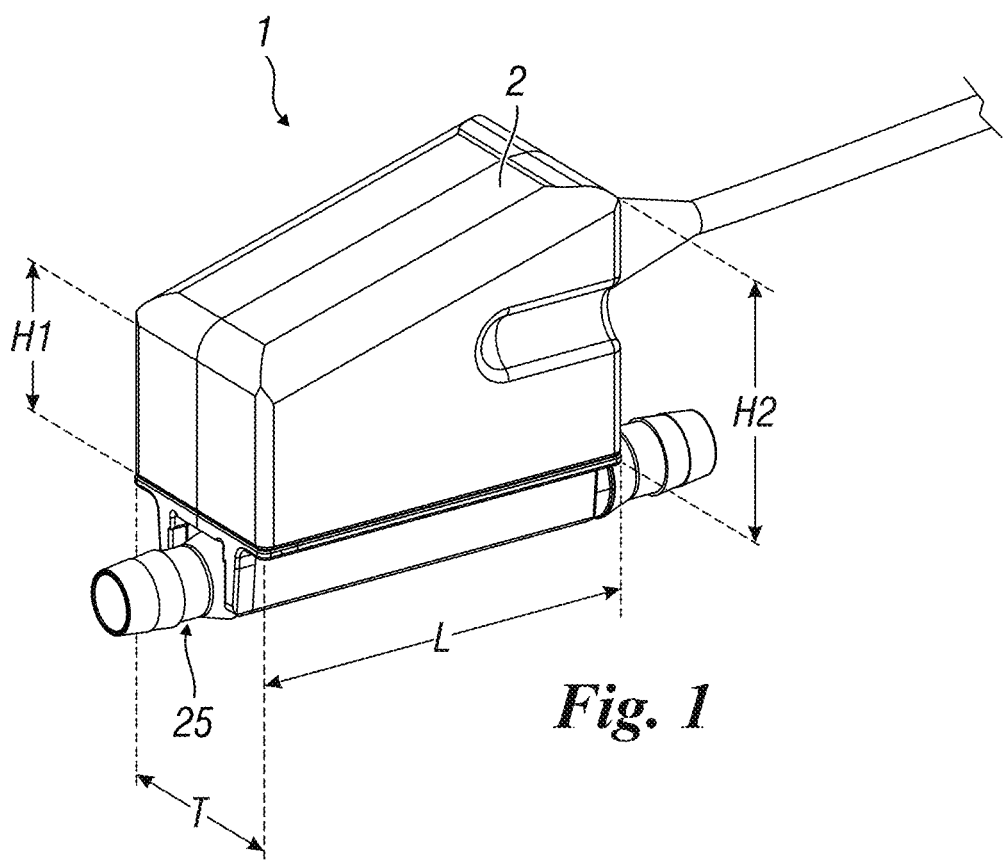
FIG. 1 illustrates a device for measuring a plurality of blood parameters in accordance with a first embodiment of the invention; the device is shown coupled to a cuvette.
Figure 1A:
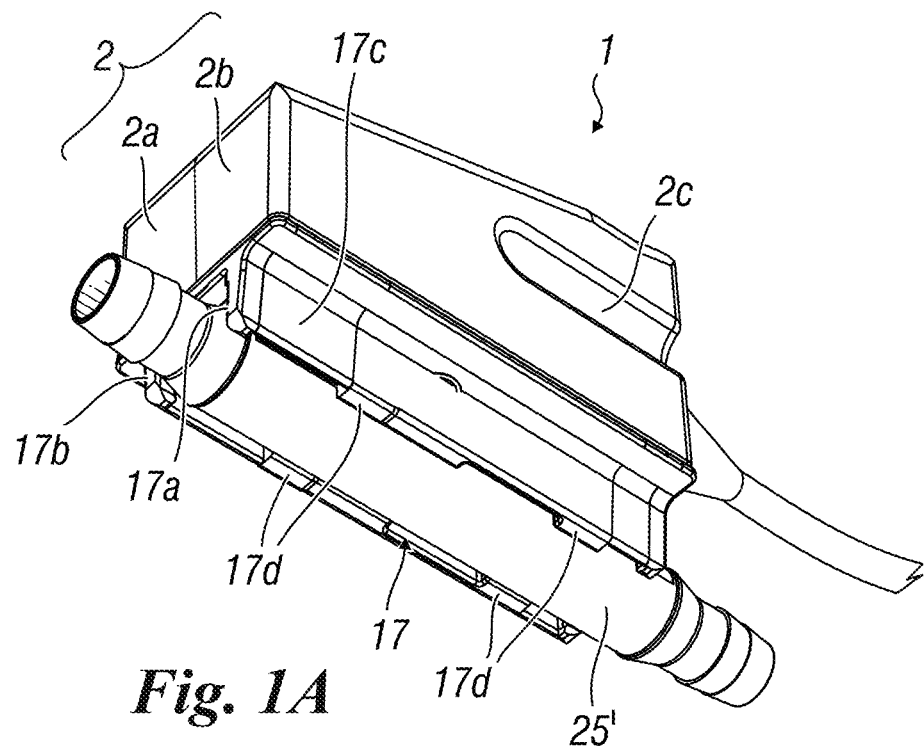
FIG. 1A illustrates a view from below of the device of FIG. 1.

Device for Measuring a Plurality of Blood Parameters

A device according to the invention is generally indicated in the figures by the numerical reference 1, 1'. The device 1, 1' is configured to measure a plurality of blood parameters, in particular the following: oxygen saturation (i.e. $SatO_2$), hematocrit (i.e. Hct), blood temperature and optionally also hemoglobin content (i.e. Hb). Preferably, the device 1, 1' is configured to measure these parameters in accordance with the following modes: measurement of oxygen saturation and hematocrit by means of artificial intelligence, measurement of temperature by means of a temperature sensor and measurement of hematocrit in a derived manner, in particular in a manner derived from the value of hematocrit; the details of the calculation of the parameters by means of artificial intelligence are set out below.

The device 1, 1' is configured to be associated with, in particular coupled to, a container 25, 25' within which blood can flow; the container 25, 25' is preferably a conduit. The container 25, 25' typically has a tubular shape and is therefore provided with a fluid passage section within which blood can flow. The container may for example be a cuvette 25 in fluid communication with an extra-corporeal blood circuit or a tube (or a portion of a tube) 25' of an extra-corporeal blood circuit. The device 1, 1' is described and depicted in accordance with a first embodiment (device indicated by numerical reference 1, see FIGS. 1-3) designed to be coupled to a tubular container such as a cuvette 25 and in accordance with a second embodiment (device indicated by numerical reference 1', see FIGS. 4-7 and FIG. 15) designed to be coupled to a tube (or a tube portion) 25' of an extra-corporeal blood circuit; clearly, further embodiments may be contemplated. The device 1, 1' and the container 25, 25' are structured to be coupled and to functionally interact with each other, as is described in detail below. The container 25, 25', being in use in contact with blood, is a disposable element, while the device 1, 1' is reusable to perform further parameter measurements. In particular, the container 25, 25' is the only disposable element of the assembly comprising the device 1, 1' and the container 25, 25'. Common features between the first and second embodiments are described herein, while their differences are also detailed below.

The device 1, 1' comprises a box body 2. The box body 2 has an internal volume in which the components described below are housed, including a control unit 3. The box body 2 has small dimensions, which provide compactness to the device 1, 1'. It should also be noted that the box body 2 may be assemblable; in particular, it may comprise two portions 2a, 2b which, under operating conditions of the device 1, 1', are assembled together. As illustrated in the attached figures, the assemblable portions may be half-shells 2a, 2b; the half-shells are preferably substantially symmetrical to each other.

The device 1, 1' comprises at least one excitation member 4, 5 configured to excite a flow of blood with electromagnetic radiation of a plurality of determined wavelengths. The electromagnetic radiation is intended to cause a light response of the blood; in this regard, see the wavelengths described below. Under operating conditions of the device 1, 1', in which the at least one excitation member 4, 5 excites the blood, the blood responds to the excitation by retro-reflecting and diffusing electromagnetic radiation comprising radiation in the visible wavelengths (light). The wavelengths are selected in such a way that the blood responds to these wavelengths with a significant light response.

The wavelengths of blood excitation can be as follows:
- 660 nm, selected because it is at this wavelength that most absorption of oxygenated hemoglobin occurs, i.e. at which the difference in absorption between the oxygenated form of hemoglobin and the non-oxygenated or reduced form is greatest,
- 805 nm, selected because the isosbestic point of hemoglobin occurs (i.e. where the absorption of oxygenated and deoxygenated hemoglobin is equal),
- 1450 nm, selected because at this wavelength there is greater absorption of water (for measuring hematocrit),
- 940 nm, selected because at this wavelength the maximum diffusion on water and maximum absorption on blood with high hematocrit occurs (it is used in conjunction with the 525 nm, 1450 nm and 805 nm wavelengths for detecting the following states of device operation: presence of blood in the container, presence of saline solution, absence of the container),
- 525 nm, selected because at this wavelength there is maximum absorption from the blood (used to determine that the device is 'seeing' blood),
- optionally, 1050 nm, selected for possible hemoglobin variation,
- optionally, 1550 nm, selected to improve the accuracy of hematocrit measurement for Hct % values lower than 40% as at this wavelength there is a greater dynamic of variation in optical counts.

The wavelengths are to be understood as belonging to a determined range around the above value, e.g. as follows:
- 660±10 nm,
- 805±5 nm,
- 1450±30 nm,
- 940±10 nm,
- 525±10 nm,
- 1050±10 nm,
- 1550 nm±10 nm.

As illustrated in the attached figures, the device 1, 1' comprises a first excitation member 4 configured to excite blood flow at least at a first plurality of wavelengths and a second excitation member 5 configured to excite blood flow at a second plurality of wavelengths. The first excitation member 4 and the second excitation member 5 are arranged within the box body 2; in particular, they are arranged side by side.

The device 1, 1', by means of the one or more excitation members 4, 5, is advantageously able to excite the blood with radiation ranging from the visible region (excitation at 600 nm) to the infrared so as to "interrogate" the blood flowing within a container 25, 25' associated with the device 1, 1' at these electromagnetic wavelengths and obtain the appropriate responses for the calculation of a plurality of parameters.

In the embodiments illustrated herein, the first excitation member 4 is configured to excite blood flow at the following wavelengths: 525 nm, 940 nm, optionally 1050 nm and the second excitation member 5 is configured to excite blood flow at the following wavelengths: 660 nm, 805 nm, 1450 nm. In further detail, each excitation member 4, 5 comprises a plurality of individual LED elements (not illustrated in the attached figures) configured to emit light radiation at a respective wavelength between said wavelengths. In particular, each excitation member 4, 5 comprises a plurality of individual LED elements in a number equal to said wavelengths that the excitation member is configured to emit.

In the embodiments disclosed herein, the first excitation member comprises a tricolour LED member 4 configured to excite blood flow at 525 nm, 940 nm, optionally 1050 nm (first plurality of wavelengths) and the second excitation member comprises a Multiwavelength LED member 5 configured to excite blood flow at 660 nm, 805 nm, 1450 nm (second plurality of wavelengths). Each excitation member 4, 5 comprises a chip on which individual LED elements are mounted; the tricolour LED member 4 mounts three LED elements to emit electromagnetic radiation wavelengths of 525 nm, 940 nm and 1050 nm and the Multiwavelength LED member 5 mounts at least three LED elements to emit electromagnetic radiation at wavelengths of 660 nm, 805 nm, 1450 nm. Optionally, the Multiwavelength LED member 5 also mounts a fourth LED element to emit electromagnetic radiation also at the wavelength of 1550 nm; this LED element can be used to improve the measurement accuracy of the hematocrit, in particular for hematocrit values below 40%).

The individual LED elements can be activated (switched on), by the control unit 3, in a time-controlled manner, as follows: switch-on order every 100 us with a frequency of approximately 20 pulses per second, then turned off 50 ms. The LED elements are switched on one at a time and within 1 second there are 20 optical count measurements transmitted per LED element (per light source). Preferably, all LED elements are switched on at the same frequency. In this time, these measurements are averaged for each individual LED element, and the ratio of the optical counts is calculated, which is used (as will be seen below) for the calculation of the parameters. The Applicant noted that such timings allow for a good signal-to-noise ratio, to the benefit of the parameter measurements to be made. Clearly, other timings permitting a good signal-to-noise ratio and/or an optimal measurement of the parameters may be used.

In order to protect each excitation member 4, 5, the device 1, 1' may provide an appropriate excitation member protection window 6, 7. Each excitation member protection window 6, 7 is intended to protect the respective excitation member 4, 5 from electromagnetic waves of frequencies different from the frequencies which the respective excitation member 4, 5 can emit; the device 1, 1' shown in the attached figures has a first and a second excitation member protection window 6, 7 intended to protect the first and the second excitation member 4, 5 respectively (see FIGS. 2 and 7). The protective windows 6, 7 of the excitation member are facing the respective excitation member 4, 5 in such a manner that, in use, they are arranged between the respective excitation member 4, 5 and the container 25, 25' into which blood flows (see FIG. 3). Each excitation member window 6, 7 may be made of material configured to pass radiation of the frequencies that the respective excitation member 4, 5 is configured to emit; for example, each excitation member window 6, 7 may be made of COP (Cyclo Olefin Polymer).

The device 1, 1' further comprises at least one electromagnetic radiation detecting member 8, 9 configured to detect a plurality of electromagnetic blood responses comprising electromagnetic radiation or light retro-reflected or diffused by the blood. The electromagnetic radiation, including light responses, are retro-reflected or diffused from the blood under operating conditions of the device following excitation by the one or more excitation members 4, 5.

In greater detail, as illustrated in the attached figures, the device 1, 1' comprises a first electromagnetic radiation detection member 8 and a second electromagnetic radiation detection member 9. In the embodiments described herein, each electromagnetic radiation detection member is in the form of a photodetector 8, 9; therefore, the following description refers to the electromagnetic radiation detection members as photodetectors (photodiodes). It is understood that the device 1, 1' may comprise one or more electromagnetic radiation detecting member(s) different from the photodetectors 8, 9.

The device 1, 1' thus comprises a first photodetector 8 and a second photodetector 9, each of which is configured to detect a plurality of blood light responses. The first photodetector 8 and the second photodetector 9 are arranged within the box body 2; in particular, they are arranged side by side.

The first and second photodetectors 8, 9 are configured to detect the blood response at a respective plurality of different wavelengths. The first photodetector 8 is preferably configured to detect the light response of the blood upon excitation at the following wavelengths: 660 nm, 805 nm, 525 nm, 1050 nm, 940 nm. As for the second photodetector 9, it is preferably configured to detect the light response of the blood upon excitation at the following wavelengths: 805 nm and 1450 nm.

In the embodiments disclosed herein, the first photodetector is preferably a Si (Silicium) type photodiode 8, i.e., it is a silicon photodiode, and the second photodetector is preferably an InGaAs (Indium Gallium Arsenide) type photodiode 9, i.e., it is a semiconductor composed of indium, gallium and arsenic that is typically sensitive to the electromagnetic radiation band between 600 nm and 2600 nm.

In terms of operation, each photodiode 8, 9 converts the electromagnetic radiation it receives into an electrical signal (current), via transimpedance the current is converted into a voltage, which is amplified by an analogue-to-digital converter (ADC, part of control unit 3) that detects a number between 0 and 4096 corresponding to the detected optical counts. These optical counts are used by the control unit 3 to calculate ratios, as will be seen in more detail below. The ratios of optical counts are shown in the attached FIGS. 10 and 11 as "ratios".

In order to protect each photodetector 8, 9, the device 1,1' may provide a respective photodetector protection window 10, 11. Each photodetector protection window 10, 11 is intended to protect the respective photodetector 8, 9 from electromagnetic waves of frequencies different from the frequencies which the photodetector 8, 9 can detect; the device 1, 1' shown in the enclosed figures has a first and a second photodetector protection window 10, 11 intended to protect the first and the second photodetector 8, 9 respectively (see FIGS. 2 and 7). The photodetector protection windows 10, 11 face the respective photodetector 8, 9 in such a manner that, in use, they are arranged between the respective photodetector 8, 9 and the container 25, 25' into which blood flows (see FIG. 5A). Each photodetector protection window 10, 11 may be in material configured to pass radiation of the frequencies that the respective photodetector 8, 9 is configured to detect; for example, each photodetector protection window 10, 11 may be in COP (Cyclo Olefin Polymer), i.e., in the same material as the protection window 6, 7 of excitation member.

The device 1, 1' comprises a temperature sensor 12 housed within the box body 2 and configured to detect the temperature of blood. In particular, the temperature sensor 12 is configured to detect the temperature of the blood inside the container. To enable easy detection of the temperature of the blood contained in the container 25, 25', the temperature sensor is preferably arranged in proximity to a coupling portion of the device 1, 1' configured to enable coupling with the container 25, 25'. Even more particularly, the temperature sensor 12 is disposed in proximity to the coupling portion such that it faces the container 25, 25' in the coupled configuration of the device 1, 1'. The temperature sensor is preferably an infrared temperature sensor 12.

In order to protect the temperature sensor 12, the device 1, 1' may provide a temperature sensor protection window 13. The temperature sensor protection window 13 is intended to protect the temperature sensor 12 from electromagnetic waves of frequencies different from the frequencies that the temperature sensor 12 can detect. The temperature sensor protection window 13 is facing the temperature sensor 12 in such a manner that, in use, it is arranged between the temperature sensor 12 and the container 25, 25' into which blood flows (see FIGS. 3 and 5A). In the embodiment in which the temperature sensor 12 is of the infrared type, the temperature sensor protection window 13 may be made of material configured to pass radiation in the infrared frequency; for example, the temperature sensor protection window 13 may be made of zinc sulphide (ZnS).

The box body 2 comprises at least one aperture 14 suitable for facing, under operating conditions of the device 1, 1', the container 25, 25' into which blood flows. The excitation and electromagnetic radiation detecting members are facing the aperture or a respective aperture such that they can respectively excite the blood and receive excitation responses from the blood. Also the temperature sensor is preferably facing the container so that it can measure the temperature of the blood. An opening 14 for each member 4, 5, 8, 9 and an opening for the temperature sensor 12 can be provided (see FIG. 4). In accordance with the embodiments shown, the electromagnetic radiation detection members 8, 9 are arranged between the excitation members 4, 5 and the temperature sensor 12. Furthermore, as shown, the excitation members 4, 5, the electromagnetic radiation detection members 8, 9 and the temperature sensor 12 may be aligned along the same longitudinal direction. Such features relating to the structural arrangement of the excitation members 4, 5, the electromagnetic radiation detection members 8, 9 and the temperature sensor 12 increase the compactness of the device 1, 1'.

In the following, structural and functional differences between device 1 according to the first embodiment and device 1' according to the second embodiment are described, and then the operating logic of control unit 3 of the device 1, 1' is described. The functional differences relate to the modes of engagement between the devices 1, 1' and container (cuvette 25 and tube 25' respectively) to which they are configured to be coupled.

First Embodiment of the Device (Device that can be Associated with a Cuvette)

The first embodiment of the device 1 was conceived to operate on a cuvette 25 into which, during measurement, blood circulating in an extracorporeal blood circuit flows. The cuvette 25 has a flat surface, in particular a flat top surface, defining a flat reading area necessary for the accuracy of the measurement; see FIG. 2.

The box body 2 also has an opening 15 suitable to allow connection with a cable 16; the cable 16 allows the transmission of digital data, processed by the control unit 3, to a medical machine 90', 90" and/or to a display means 91. The cable 16 also enables the power supply of the device 1. As illustrated in the annexed figures, the cable 16 may have a strain-release element 16a capable of avoiding or minimizing strain at the portion of the cable 16 passing through the box body 2. The box body 2 has at least one grip portion 2c, capable of enabling the device 1 to be easily gripped and handled; as illustrated in the annexed figures, the grip portion may be in the form of a pair of grooves 2c defined on opposing sides of the box body 2.

Geometrically, the box body 2 has a length L, a width T and a height H; the width T is preferably smaller than the length L and the height H. The box body 2 preferably has a conformation such that the necessary components of the device 1 are accommodated therein in the smallest possible volume. As illustrated in the attached figures, the height H may vary along the length L; the box body 2 may therefore have a minimum height H1 and a maximum height H2, which may be defined at the respective opposite ends to the length L of the box body 2. The length L, measured along the prevailing direction of the container, may be between 40 and 80 mm. The width T, measured orthogonally to the length L, may be between 15 and 50 mm. The height H, measured orthogonally to the length L and the width T, may be between 30 and 80 mm. In essence, the device 1 has dimensions such that it is substantially pocket-sized. By way of non-limitation, it should be noted that, in the preferred version of the first embodiment, the length L may be 65 mm, the maximum height H2 may be 58 mm and the width L may be 35 mm. In the first embodiment, the volume of the box body 2 defines the volume of the device 1; the volume of the device 1 may be within the volumes that can be calculated from the extremes of the above-mentioned dimensional ranges. In particular, in possible embodiments, the volume of device 1 may be between 20,000 mm$^3$ and 400,000 mm$^3$, optionally between 50,000 mm$^3$ and 200,000 mm$^3$, more specifically between 75,000 mm$^3$ and 175,000 mm$^3$, even more specifically between 90,000 mm$^3$ and 150,000 mm$^3$.

The device 1 includes a coupling portion 17 associated with the box body 2. With reference to the orientation of the device 1 illustrated in the attached figures, the coupling portion 17 is joined to the box body 2 at a lower portion of the box body 2. The coupling portion 17 may develop parallel to the length L of the box body 2 between two opposing longitudinal ends of the box body 2. The coupling portion 17 may be integral with the box body 2. The coupling portion 17 comprises a seat 17a provided with a volume dimensioned to accommodate a container 25' for blood, in particular a cuvette. The seat may take the form of a groove 17a developed along the longitudinal direction of development of the coupling portion 17. As illustrated in the attached figures, the coupling portion 17 may be in the form of a skirt emerging from a lower portion of the box body 2 so as to delimit the seat 17a; the skirt has opposing walls 17b, 17c between which the seat 17a is defined. Since the measurement is optical, it is advantageous to shield the optically sensitive zone as much as possible from external light components; to this end, the walls are configured to shield the light and reduce the possibility of glare or direct light affecting the measurement. Each wall 17b, 17c may be integral with its respective half-shell. Each wall 17b, 17c may further comprise one or more structural elements 17d, which may be in the form of recesses and/or ribs, configured to allow unambiguous coupling between container 25 and device 1 and, additionally or alternatively, lighten (for recesses) or strengthen (for ribs) the wall 17b, 17c on which they are defined. Preferably, the walls 17b, 17c provide recesses/ribs 17d with the dual function of lightening/reinforcing the wall 17b, 17c on which they are defined and of allowing unambiguous coupling between the device 1 and a determined container 25, which may in turn have corresponding structural elements 25a. This allows the inversion of containers, such as cuvettes 25, between arterial or venous probes; in other words, this allows the device 1 described herein (arterial probe) to be uniquely coupled to an arterial cuvette due to the corresponding recesses/ribs that the latter presents, thereby preventing a venous cuvette from being coupled to the arterial probe.

Figure 2:
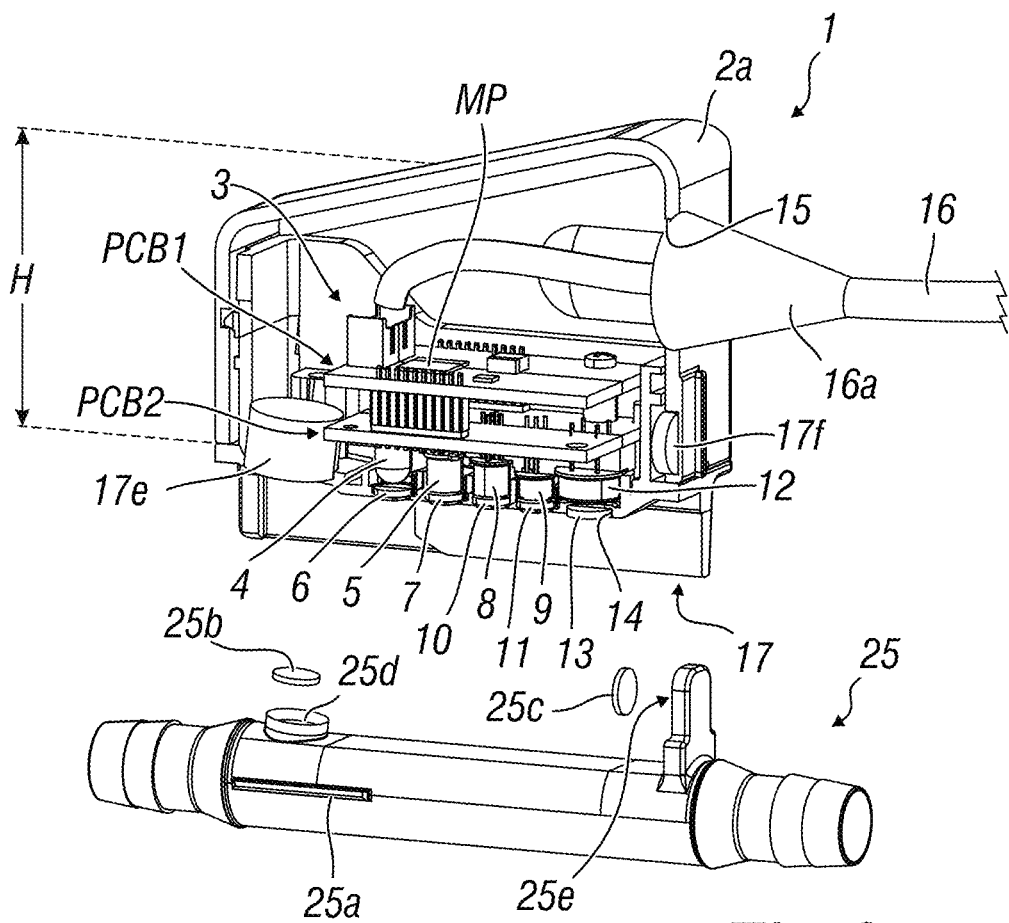
FIG. 2 illustrates an exploded view of the device and cuvette of FIG. 1 (the magnetic coupling elements of the cuvette are also shown in the exploded view), where a half-shell of the box body of the device has been removed to show the device components housed inside the box body.
Figure 3:
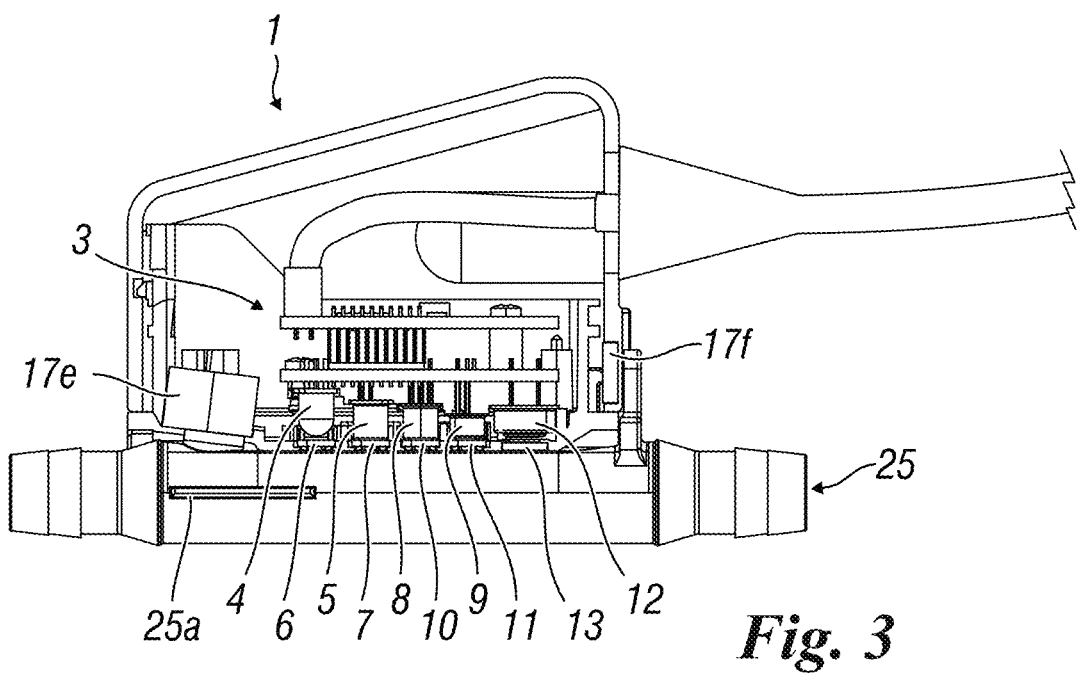
FIG. 3 illustrates the device and the cuvette of FIG. 2 in coupled conditions, so as to show the positioning of the various internal components of the device in operating conditions.
Figure 4:
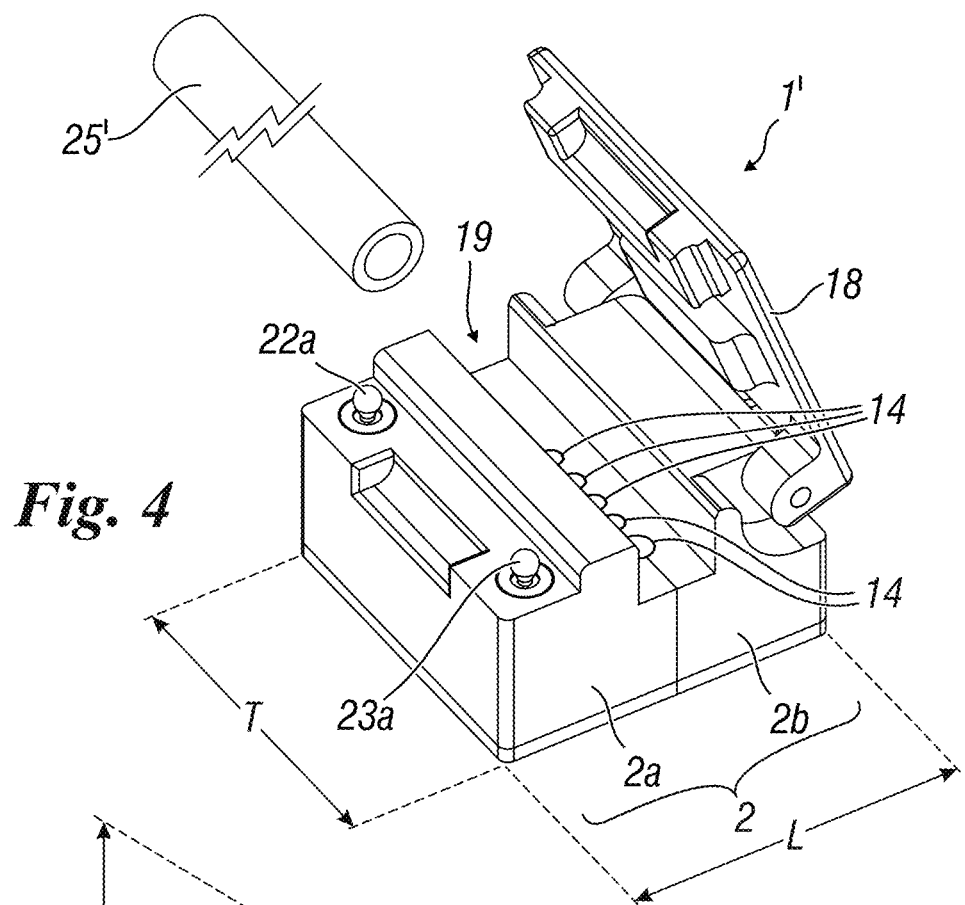
FIG. 4 illustrates a frontal perspective view of a device for measuring a plurality of blood parameters in accordance with a second embodiment of the invention and, in exploded view, a tube; the covering element of the device is in a rest configuration (opened covering element)

The coupling portion 17 comprises at least one coupling element 17e, 17f which allows the device 1 to assume a coupled configuration in which the housing 25 is coupled to the device 1 (illustrated in FIGS. 1 and 3) and a decoupled configuration in which the housing 25 is decoupled from the device 1. The measurement of the blood parameters takes place in the coupled configuration in which the container 25 is housed at the seat 17a. As illustrated in the attached figures, the coupling portion 17 may comprise at least a first coupling element 17e and a second coupling element 17f. The first and second coupling elements 17e, 17f may be longitudinally opposed to each other (see FIG. 2). The first and second coupling elements 17e, 17f are configured to couple with corresponding coupling elements 25b, 25c of the container 25. Providing two coupling elements 17e, 17f arranged in opposing positions allows for greater security and stability in the coupling between device 1 and container 25. The first and second coupling elements 17e, 27f can be of the same type; the attached FIGS. 1 to 3 show coupling elements of magnetic type. Each coupling element comprises a respective magnet 17e, 17f configured to couple to a respective and corresponding magnet 25b, 25c of the container 25 (see FIG. 2); it is noted that the magnets 25b, 25c of the container are housed at respective locations 25d, 25e. As can be seen in FIG. 2, both the magnets 17e, 17f of the device 1 and the magnets 25b, 25c of the container 25 can develop on storage planes transverse to each other. Alternative embodiments are not excluded in which at least one of the two coupling elements 17e, 17f is not magnetic but is, for example, mechanical.

The device 1 may further comprise a further temperature sensor which may preferably be a thermistor; it, not shown in the attached figures with regard to this first embodiment, may be arranged inferiorly with respect to the electromagnetic radiation detection member 9. The further temperature sensor is configured to measure the temperature of the electromagnetic radiation detecting member 9 in such a way as to monitor the temperature of said electromagnetic radiation detecting member 9 (photodiode InGaAs) in order to be able to correct the optical responsivity to changing temperature. The additional temperature sensor is in contact with the electromagnetic radiation detection member and the area confined to it.

Second Embodiment of the Device (Device that can be Associated with a Tube)

The second embodiment of the device 1' was conceived to operate directly on a portion of an extra-corporeal blood circuit tube, into which blood flows during the measurement.

Figure 5:
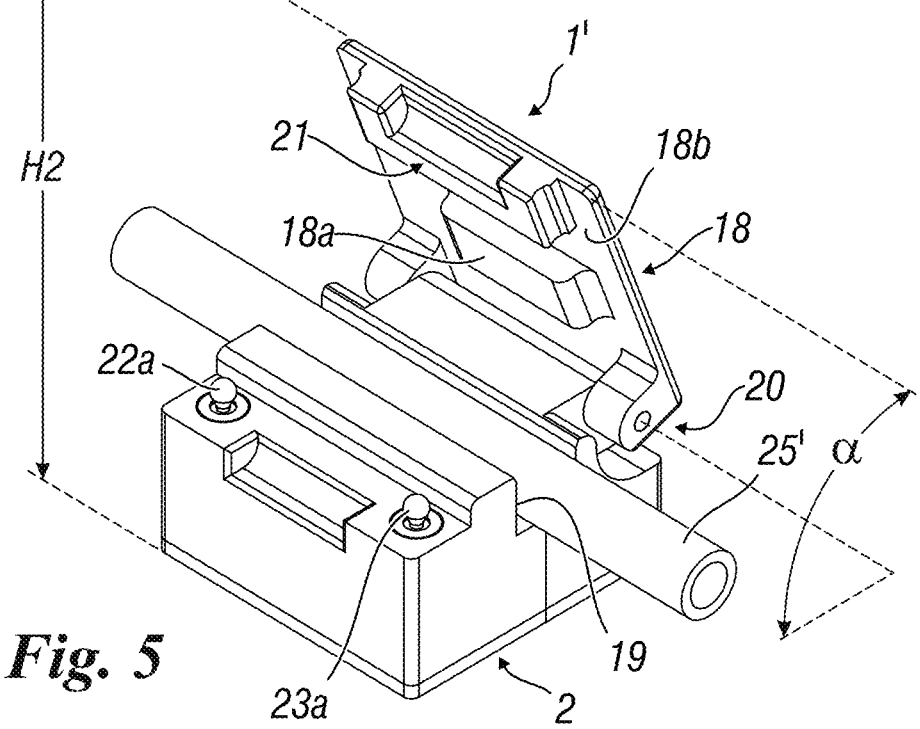
FIG. 5 illustrates the device in FIG. 4 with the tube engaged at the appropriate seat.
Figure 5A:
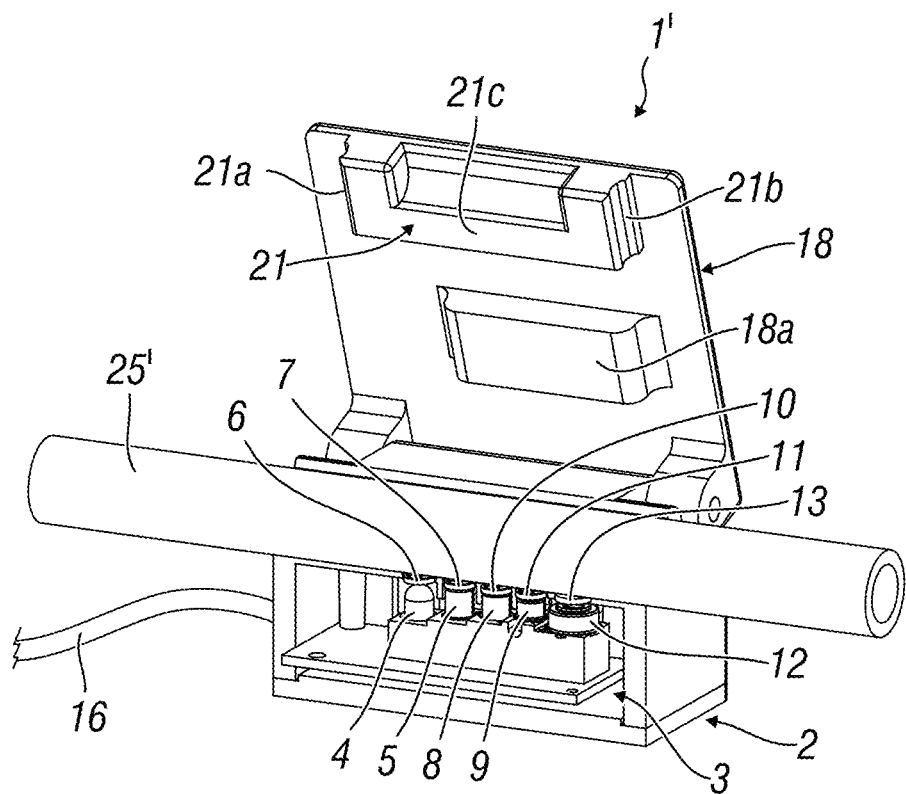
FIG. 5A illustrates the device and tube of FIG. 5, where a half-shell of the box body of the device has been removed to show the device components housed inside the box body and the positioning of said components in operating conditions.
Figure 6:
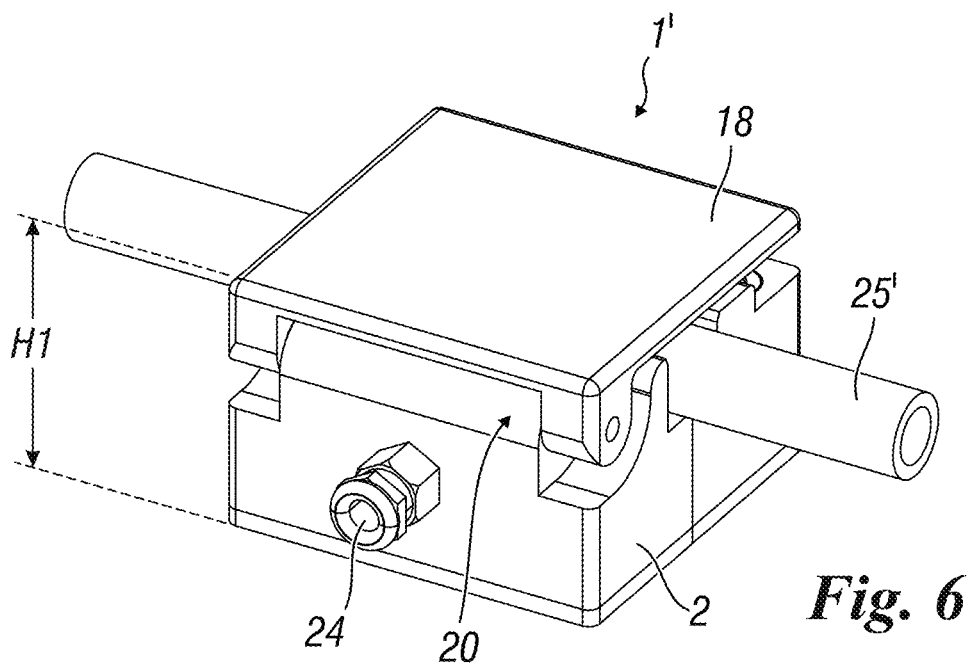
FIG. 6 shows a rear perspective view of the device of FIG. 4 in which the tube is engaged at the seat and the covering element is in the operating configuration (closed covering element)

The device 1' comprises a covering element 18, 18' movable relative to the box body 2 and a seat 19. As previously mentioned, the box body 2 is the portion providing housing for the excitation members 4, 5, the electromagnetic radiation detection members 8, 9 and the control unit 3. The box body 2 of the device 1' may have, in addition to the two half-shells 2a, 2b, also a base portion 2d suitable for connecting the two half-shells 2a, 2b by means of constraining elements 2e, such as threaded elements. The seat 19 is defined at a coupling portion of the box body 2 and is adapted to accommodate a portion of the tube 25' of an extra-corporeal blood circuit. The covering element 18, 18' is configured to operate at least between an operative configuration (closed configuration of the covering element, see FIGS. 6 and 6A) in which it flattens opposing surfaces of the tube 25' housed at the seat 19 and a rest configuration (open configuration of the covering element, see FIGS. 5 and 5A), to which corresponds a respective position of the covering element 18, 18' relative to the box body 2. In essence, the covering element is a closing element capable of being moved between a closed position and an open position. As illustrated in FIGS. 5 and 6, the covering element 18, 18' is hinged to the box body 2 at a hinging portion 20 of the device 1 and is movable by rotation relative to the box body 2 in such a way as to determine the transition between positions corresponding to the rest configuration and the operative configuration. The covering element 18, 18' can rotate with respect to the box body 2 by an angle $\alpha$, $\alpha'$, $\alpha''$; the angle $\alpha$, $\alpha'$, $\alpha''$ can be defined as the angle defined by a main body 18b of the covering element 18, 18' with a horizontal plane (see FIGS. 5, 17 and 18). The box body 2 and the covering element 18, 18' may present the same footprint in plan, in particular a polygonal footprint, in particular a quadrilateral footprint; in the annexed figures, both the box body 2 and the covering element 18, 18' present a substantially square footprint in plan (see FIGS. 4-7 and FIG. 15); such a conformation ensures compactness to the device and minimises its footprint. Further structural and geometric details follow.

In this second embodiment, it is important that the upper and lower surfaces of the tube 25' are, during measurement, at least partially flat for the correct functioning of the device 1' and, above all, measurement repeatability and accuracy; to allow this, the seat in which the tube 25' fits and the covering element 18, 18' are designed in such a way as to obtain the "rectangular" tube section/shape (see FIG. 6A) by flattening the surfaces of the tube 25' (note that such flattening is not necessary for the cuvette 25 because it includes a flat surface defining the flat reading area; see FIG. 2). Having a flat reading area during the measurement allows the emission cone of the electromagnetic radiation from the individual LED elements to enter the tube as far as possible without interacting with the walls and altering their transmission.

Figure 15:
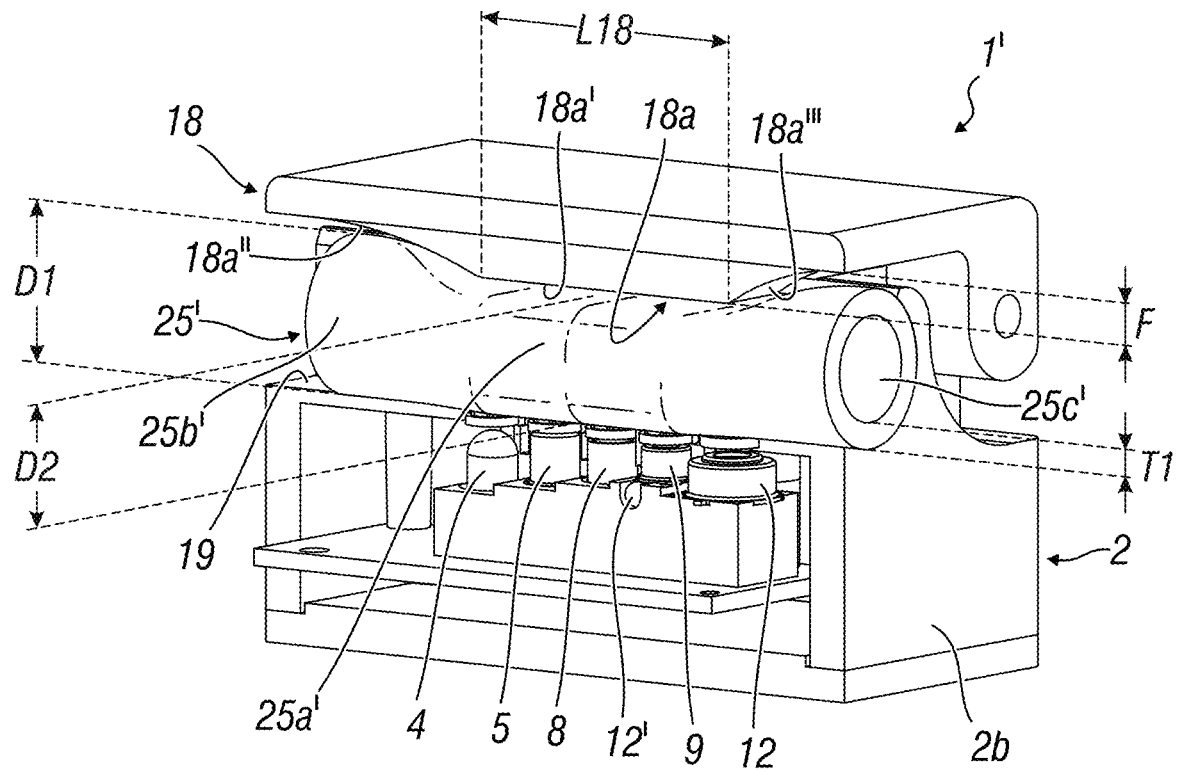
FIG. 15 illustrates a crushing profile of the tube relative to the configuration of FIG. 6A; it shows in more detail how the covering element compresses the tube, resulting in a smooth transition between uncompressed portions of the tube and the central portion of the tube that is compressed at the seat to obtain a flat reading area.

The covering element 18, 18' includes a compression element 18a for compressing, in the operative configuration, the portion of the tube 25' housed therein. The compression element 18a is engaged to the main body 18b of the covering element 18, 18'. The compression element 18a compresses the tube 25' at the measuring zone to make the reading area flat. In essence, when the tube portion 25' is inserted into the seat 19 and the covering element 18, 18' is closed, the tube portion 25' is squeezed by the compression element 18a, thereby creating two parallel flat surfaces: one in contact with the covering element 18, 18' and one in contact with the bottom of the seat 19 (see FIG. 6A). The compression element 18a has a geometric shape designed in such a way that the deformation of the portion of the tube 25' is as small as possible in order not to appreciably alter the flow of blood and thus to avoid the risk of triggering haemolytic phenomena in the blood caused precisely by abrupt changes in the section through which it flows. For this purpose, it was envisaged that the compression element 18a could realise a smooth transition from the circular shape of the tube (defined at the uncompressed portions 25b', 25c' of the tube, see FIG. 15) to the rectangular shape (defined at the compressed portion 25a' of the tube 25'; see FIG. 6A) so as to realise the minimum possible deformation aimed at minimising or even eliminating the effects due to the mechanical trauma (e.g. due to an abrupt section shrinkage) that the cellular elements, in particular the red blood cells, undergo during extracorporeal flow. Such mechanical trauma can lead to cell lysis or various forms of sub-lethal damage, including changes in cell morphology and cell deformability, release of certain cellular components and reduced cellular lifespan. Damage may result from direct contact with a solid surface or as a result of physical forces exerted on cells. The extent of the latter damage depends on the magnitude of the shear stress to which cells (particularly red blood cells) are exposed, but not on the nature of the flow regime, whether laminar or turbulent. The embodiment of the device 1' that has been conceived is such that it does not trigger damage phenomena, i.e. it remains under operating fluid dynamic conditions in the 'sub-hemolytic' zone (shear stresses well below 100 Pa), i.e. in the zone where only the interaction effects with the materials of the blood contact surfaces dominate. To this end, a determined geometric shape was provided for the compression element 18a, which allows for a gentle crushing of the tube 25'; in essence, the compression element 18a compresses a central portion 25a' of the tube 25' (portion of the tube 25' dislocated at the seat 19) to obtain a flat reading area and determines a smooth transition between uncompressed portions of the tube 25b', 25c' among which the central compressed portion 25a' is defined; in this regard, see FIG. 15, wherein is shown a piece of tube 25' that is engaged at the seat 19 and partially compressed. FIG. 15 shows how the compression of tube 25' to obtain a flat reading area takes place at the upper surface of tube 25'; the surfaces that are flattened are both the upper and lower surfaces of the tube. In order to guarantee an optimal flattening of the tube 25' that does not compromise the characteristics of the blood (avoiding phenomena of hemolysis), the compression element 18a comprises a flat portion 18a' defined between opposed curvilinear portions, in particular ends, 18a'', 18a''', which may present a development that is analogous or similar to each other; the flat portion 18a' is apt to derive a flat reading area. The flat portion 18a' is substantially rectilinear and may have a length L18 and a depth F; the depth F may correspond to a compression entity of the tube (or crushing entity, i.e., difference between the diameter D1 of the non-deformed tube with the diameter or equivalent diameter D2 of the deformed tube). The depth F may be 2 mm. The length L18 is preferably between 10 and 50 mm, in particular between 12 and 45 mm. In the embodiment shown in FIG. 15, the length L18 is 30 mm; in another embodiment, it may be 15 mm. The tube 25' has a diameter D1 (undeformed diameter), a diameter or equivalent diameter D2 (compressed diameter) and a thickness T1 (wall thickness). Compression of the central portion 25a' of the tube 25' by the compression element 18a results in a reduction in the cross-sectional area of blood passage (caused by a decrease in the diameter of the tube 25' at length L18) of between 9% and 17%. For example, if the tube 25' has an undeformed diameter D1 of 14.3 mm, the reduction in the cross-sectional area of blood passage may correspond to a compression of the tube of approximately 14%, with a corresponding compressed equivalent diameter D2 (D2 can be defined as compressed equivalent diameter because the shape of the tube after compression is no longer circular) of the tube 25' of 12.3 mm. It should be noted that in the embodiment of FIG. 15, the diameter D1 of the tube 25' is equal to 9/16" (dimension in inches, corresponding to approximately 14.3 mm), the thickness T1 is equal to 3/32" (dimension in inches, corresponding to approximately 2.38 mm) and the equivalent diameter D2 is approximately equal to 12.3 mm; consequently, the compression entity of the tube 25' is approximately 2 mm (difference between the non-deformed diameter and the deformed diameter, equal to approximately 14% as described above). The crushing effect visible in FIG. 6A and FIG. 15 has a dual purpose: to lock the reciprocal position between the device 1' and the tube 25' and to create a substantially flat or level surface on which to perform the measurement. As shown in the attached figures, the compression element may include a protrusion 18a developing along a main longitudinal direction and provided with the outline described above.

The device 1' may further comprise a closure portion 21 capable of cooperating with the box body 2 to maintain the covering element 18, 18' in the operative configuration (closed position). The closure portion 21 may be monolithic with the covering element 18, 18' and/or may have opposing operative ends 21a, 21b. Each operative end 21a, 21b is provided with a seat, preferably defined at an outer flank of the operative end 21a, 21b; the seat may be a groove, for example with a curvilinear profile. The closure portion 21 may develop longitudinally parallel to the compression element 18a. In the embodiment illustrated (see FIGS. 5 and 5A), the closure portion 21 is in one piece and has opposing operative ends 21a, 21b and connected by an intermediate portion 21c. The closure portion 21 is easily cleaned as it has no recesses that are difficult to access and/or difficult to clean.

The device 1' preferably comprises at least one constraint element 22, 23 configured to keep the covering element 18, 18' in the operative configuration; in essence, the constraint element 22, 23 allows the covering element 18, 18' to be kept closed when it is in the operative configuration (during parameter measurement). As illustrated in the attached figures, the device 1' preferably comprises two constraint elements 22, 23 configured to keep the covering element 18, 18' in the operative configuration. The constraint elements 22, 23 are engaged to the box body 2 in the vicinity of an upper surface of the box body 2 and at respective locations 2f defined on the box body 2. The two constraint elements 22, 23 are opposed to each other, so as to ensure a stable and symmetrical closure; furthermore, the symmetry of the closure helps to ensure that the defined measuring surfaces at the reading area are flat. In order to effect a stable closure of the covering element 18, 18', the constraining elements 22, 23 are preferably opposed to the hinge portion 20. As illustrated in the appended figures, each constraining element 22, 23 may provide a movable element 22a, 23a, for example having a curved head (e.g. at least partially spherical); upon closing, each movable element 22a, 23a may be moved by the opposing operative ends 21a, 21b of the closing portion 21; such movement determines the engagement of the constraining elements 22, 23 with their respective seats. This engagement is preferably determined by the housing of the curved head 22a, 23a of each constraining element 22, 23 at the curved groove of a respective operative end 21a, 21b of the closure portion. The movement of the constraining elements 22, 23 preferably takes place in reciprocal movement away from each other. Each movable element 22a, 23a can be moved at least in the direction that determines the constraint with the closure portion 21 (external direction, moving away from each other), in particular it can be moved in a plurality of directions, preferably substantially in each direction. The movable elements 22a, 23a are substantially hermetic; therefore, providing that the closure of the covering element 18, 18' is realised by means of substantially hermetic movable elements 22a, 23a and by means of the easily cleanable closure portion 21 guarantees, in addition to a stable closure, a high cleanability of the device 1'; this is clearly advantageous from a hygienic point of view.

The box body 2 also has a provision 24 for connection (preferably a connector) to enable connection with a cable 16; the cable 16 enables transmission of digital data, processed by the control unit 3, to a medical machine 90', 90" and/or to a display means 91. The cable 16 also enables the power supply of the device 1'. As illustrated in the attached figures, the provision 24 for connection can be provided in the vicinity of the hinge portion 20, in particular at a flank of the box body 2 and below the hinge portion 20.

Figure 7:
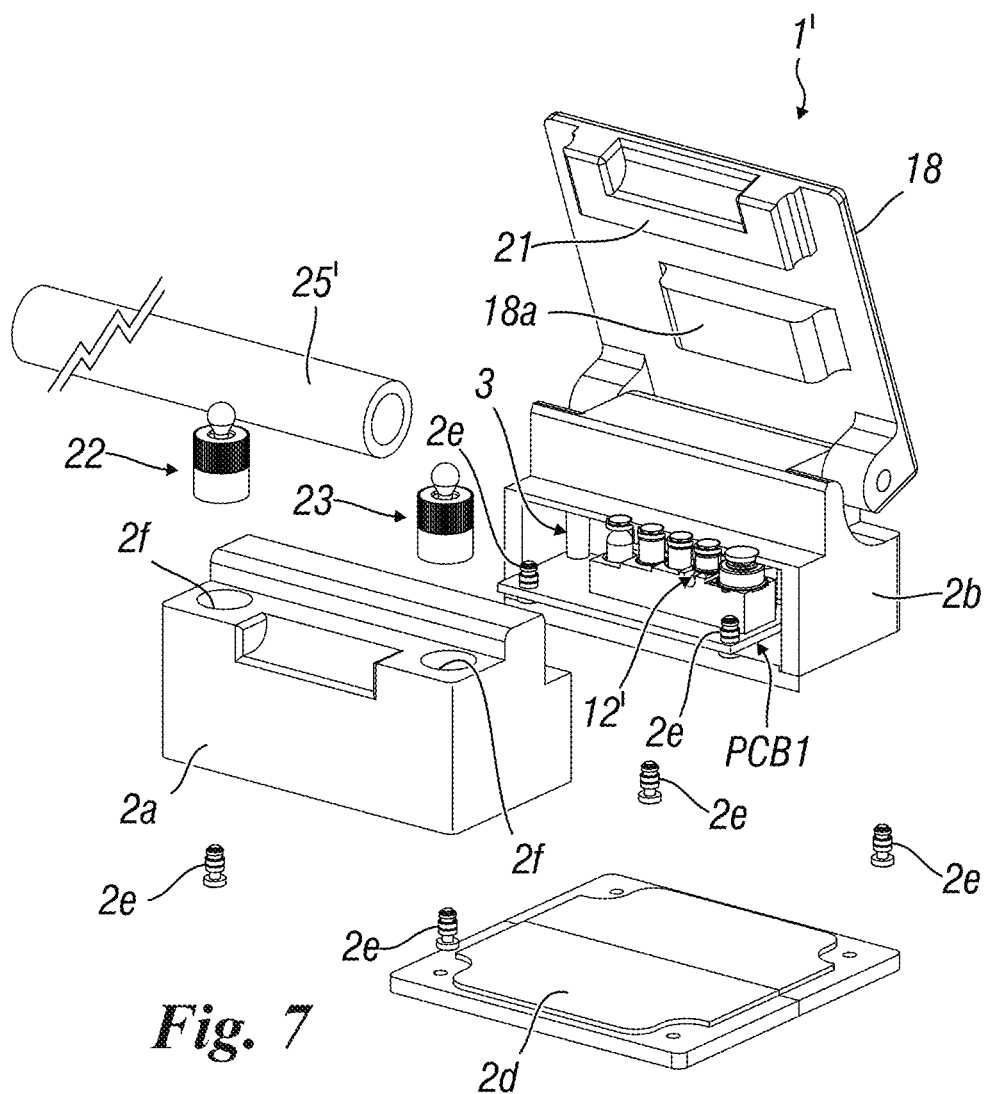
FIG. 7 illustrates an exploded view of the device and the tube of FIG. 4.

The device 1' may further comprise an additional temperature sensor 12' which may preferably be a thermistor (see FIG. 7). The further temperature sensor 12' is configured to measure the temperature of the electromagnetic radiation detecting member 9 so as to monitor the temperature of said electromagnetic radiation detecting member 9 (InGaAs photodiode) in order to be able to correct the optical responsivity to changing temperature. The additional temperature sensor 12' is in contact with the electromagnetic radiation detection member 9 and with the area confined thereto.

Geometrically speaking, the device 1' has a length L, a width T and at least one height, in particular a minimum height H1 and a maximum height H2; in the illustrated embodiment, the width T is substantially comparable to the length L (essentially square outline). Width T and length L are dimensions referred to box body 2, while heights H1, H2 are dimensions defined in cooperation between box body 2 and covering element 18, 18'. The box body 2 preferably has a conformation such that the necessary components of device 1' can be accommodated therein in the smallest possible volume. As illustrated in the enclosed figures, the height H1, H2 of the device 1' is a function of the configuration assumed by the covering element 18, 18'; the box body 2 may therefore present a minimum height H1 (height with covering element in operating configuration) corresponding to the conditions of use of the device 1' and a maximum height H2 (height with covering element in rest configuration) corresponding to the rest conditions of the device 1'. The length L may be between 40 and 80 mm. The width T, measured orthogonally to the length L, may be between 40 and 85 mm. The minimum height H1, measured orthogonally to length L and width T, may be between 30 and 60 mm. In essence, the device 1' has dimensions such that it is substantially pocket-sized. By way of non-limitation it should be noted that, in the preferred version of the second embodiment, the length L may be 64 mm, the minimum height H1 may be 44 mm, and the width L may be 67 mm; the length L and width T being similar values, the box body 3 may be substantially square-shaped (see FIGS. 4 to 7). In the second embodiment, the volume of the device 1' is defined by the box body 2 and the covering element 18, 18'; in the volumes described below, reference will be made to the volume of the device 1' calculated using the minimum height value H1 as the height value. The volume of device 1' can be included within the volumes that can be calculated from the extremes of the dimensional intervals described above. In particular, in possible embodiments, the volume of device 1' may be between 48,000 mm$^3$ and 408,000 mm$^3$, optionally between 75,000 mm$^3$ and 330,000 mm$^3$, more specifically between 120,000 mm$^3$ and 260,000 mm$^3$, even more specifically between 150,000 mm$^3$ and 220,000 mm$^3$. The above-described quadrilateral conformation, in particular substantially square, is the minimum one to encompass the physical dimensions of the components (including the constraining elements 22, 23 and the closure portion 21).

This embodiment is advantageous in that it avoids the use of a component, i.e. the cuvette 25, which increases the cost of using the device 1'; moreover, the device 1' allows blood parameters to be monitored 'on the go', i.e. when the medical procedure has already started, by coupling the device 1' directly to the tube 25' of the extracorporeal blood circuit.

Figure 16:
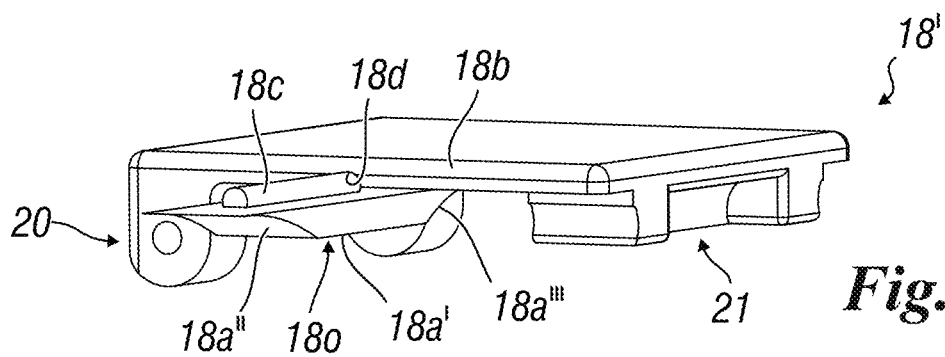
FIG. 16 shows an alternative covering element to that shown in FIGS. 4 to 7 and in FIG. 15; the compression element of this alternative covering element is configured to oscillate relative to a body of the covering element itself. The oscillating compression element is shown partially withdrawn from its seat realized in the body of the covering element.
Figure 17:
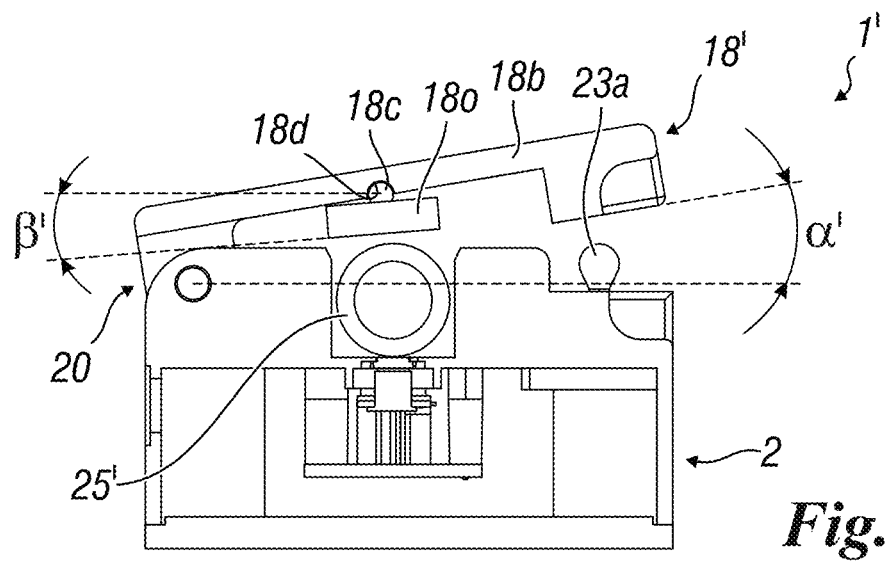
FIG. 17 shows, in cross-section, a device in accordance with a variant of the second embodiment, with the covering element assuming an angular position in which the oscillating compression element is placed close to the tube.
Figure 18:
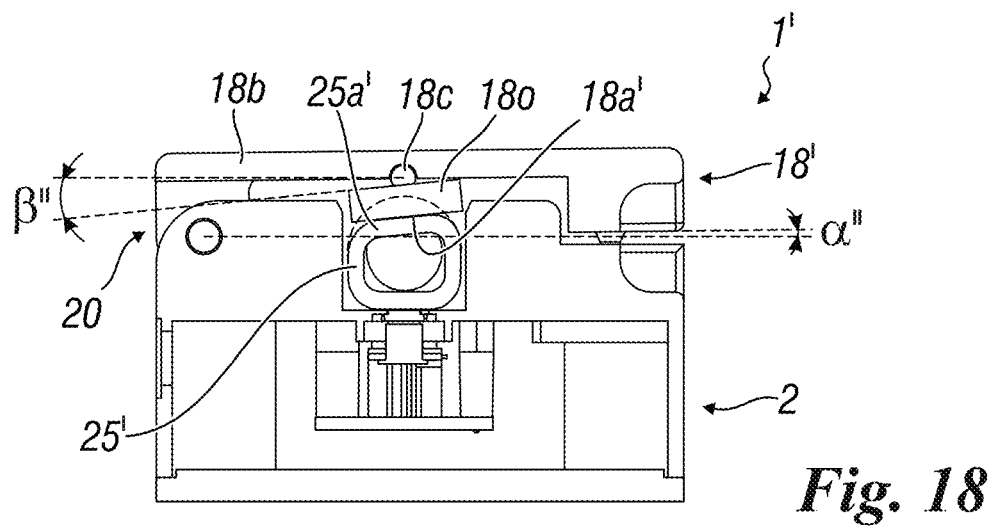
FIG. 18 shows, in cross-section, the device of FIG. 17, in which the covering element has been further rotated towards the tube from the angular position of FIG. 17 and the oscillating compression element compresses the tube.

FIGS. 16, 17 and 18 show a covering element 18' in accordance with an alternative variant to the covering element 18 shown in FIGS. 4 to 7 and FIG. 15. In accordance with this variant, the covering element 18' provides a compression element 180 configured to oscillate (tilting compression element) relative to the body 18b of the covering element 18'. Except for the ability to oscillate, the compression element 180 may have the same characteristics as the previously described compression element 18a, in particular the same conformation, and may therefore have the portions 18a', 18a'', 18a''' (see FIG. 16).

Underpinning the development of the oscillating compression element 180 is the need to achieve as smooth a blood passage cross-section as possible. By providing the possibility of adapting the compression of the tube 25', the oscillating compression element 180 enables the repeatability of measurements to be increased which, being optical in nature, should not be affected at all by the non-fixed and repeatable positioning of the tube 25' in front of the optical component protection windows previously described.

To allow oscillation of the compression element 180, the covering element 18' comprises a pin 18c housed within a corresponding seat 18d defined on the body 18b. FIGS. 16, 17 and 18 show a seat 18d countershaped to a circular profile of the pin 18c. As illustrated in those figures, the pin 18c may be made in one piece with the oscillating compression element 180; in alternative embodiments, they may form two separate but joined components. As illustrated in FIGS. 16, 17 and 18, to retain the pin 18c, the seat 18d may substantially define an undercut; in terms of assembly of the compression element 180 to the body 18b, the pin 18c may be inserted into the seat 18d (see FIG. 16). Clearly, means, such as kinematics, alternative to the pin 18c (e.g. a cam or parallelogram kinematics) may be provided to allow oscillation of the compression element 180 with respect to the body 18b or of the entire covering element 19' with respect to the housing 25'. The oscillating compression element 180 is pulled into rotation by the body 18b of the covering element 18'. Although dragged in rotation by the covering element 18', the compression element 180, thanks to the pin 18c, can assume an angular position in accordance with an angle β', β'' different from the angle α, α', α'' of the covering element 18'. In particular, two rotational configurations of the covering element 18' are visible in FIGS. 17 and 18 in which the body of the covering element 18' is positioned in accordance with a respective angle α', α'', while the compression element 18' assumes a respective and different angle β', β''. The angle β', β'' described by the compression element 180, although different from the angle α, α', α'' described by the body 18b of the covering element 18', is nevertheless related thereto in that certain angular positions of the covering element 18' correspond to corresponding angular positions of the compression element 180. The device 1' may provide that the body 18b of the covering element 18' rotates in accordance with a first direction of rotation (e.g. clockwise) with respect to the hinge portion 20 and that the compression element 180 rotates in accordance with the first direction of rotation and a second direction of rotation (e.g. anti-clockwise) opposite to the first direction of rotation; this is possible because the compression element 180 is tilting and is therefore configured to adapt, by oscillating around the pin 18c, its direction of rotation to the relative position between the covering element 18' and the tube 25'.

Proceeding to close the covering element 18' in the direction of the box body 2, the compression element 180 passes from a configuration in which it does not compress the tube 25' (see FIG. 17) to a configuration in which the compression element 180 contacts the tube 25' and oscillates, then rotates, progressively as the angle α, α', α'' decreases. Therefore, in accordance with this variant, it is advantageously envisaged that the compression element 180 progressively adapts to the conformation of the tube 25' and gently compresses the central portion 25a' of the tube 25' in such a way as not to significantly alter the flow of blood within the tube 25'. FIG. 18 shows a configuration just prior to the complete closure of the covering element 18' on the box body 2; in this figure, it can be seen that the central portion 25a' of the tube is not yet fully compressed and therefore the reading area is not yet flat. It is therefore possible to obtain the approach of the compression element 180 in an almost parallel manner despite the fact that the covering element 18' is simply hinged to the box body 2.

Control Unit of the Device

The device 1, 1' further comprises a control unit 3. The logic and characteristics of the control unit 3 described below are common to both embodiments of the device 1, 1' described above. The control unit 3 is housed within the box body 2.

The control unit 3 preferably enables the device 1, 1' to carry out the measurement of parameters without the need for initial calibration, due to the training described below. Furthermore, the control unit 3 preferably enables the device 1, 1' to perform the measurement without any interaction with processing or calculation units external to the device 1, 1'; the processing of the information and data for measuring the plurality of blood parameters is thus carried out autonomously by the device 1, 1'. In this way, there is no need for a database external to the device 1, 1'; the device 1, 1' provides within the box body 2 all the components for carrying out the measurements of the parameters of interest. The device 1, 1' is capable, by means of the control unit 3, of carrying out the measurement of the parameters on the basis of a plurality of data of previous measurements of the blood parameters carried out during previous training. This is possible because control unit 3 can provide a coded calculation model. The training is preferably carried out in the laboratory (e.g. by the supplier of the device 1, 1' on the basis of requests by the end user), on a series of devices 1L, 1L' to be trained, prior to the supply of the device 1, 1' in question. As will be further discussed below, the prior training results in learning, in particular machine learning, which the control unit 3 takes into account when measuring the parameter during clinical use. Each device 1, 1' that is produced after training a certain number of devices 1L, 1L' is calibrated in the laboratory (this aspect is detailed below), so that the end user of the device 1, 1' has an instrument immediately ready for use. Since there is no initial calibration, device 1, 1' is particularly suitable for use in emergency situations. Examples of emergency situations are those requiring treatment with an extra-corporeal membrane oxygenation machine (ECMO or Extra-Corporeal Membrane Oxygenator), i.e. cardio-circulatory support, e.g. in patients with cardiac arrest or pulmonary trauma in the most acute, and otherwise untreatable, phases of Covid-19 disease (CoronaVirus Disease 19 caused by the SARS-CoV-2 virus, hereinafter also referred to as 'Covid').

Operationally, the control unit 3 is configured to implement at least the following operations:

- controlling the excitation members 4, 5 during an excitation step in which it excites a blood flow with electromagnetic radiation at a plurality of determined wavelengths,
- receiving analogue information (read by the electromagnetic radiation detecting members 8, 9) relating to the plurality of electromagnetic and/or light responses of the blood comprising electromagnetic radiation, in particular light, retro-reflected or diffused by the blood,
- converting the electromagnetic and/or light response analog information into electro-magnetic and/or light response digital data,
- processing the digital electromagnetic and/or light response data and the actual blood temperature value via one or more neural networks NN,
- determining, as a result of the processing operation using one or more neural networks NN, the value of each parameter of the plurality of blood parameters.

To carry out these operations, control unit 3 is operatively connected to excitation members 4, 5 and electromagnetic radiation detection members 8, 9.

Moving on to a higher level of detail concerning the processing and measurement of parameters by device 1, 1', it is indicated that control unit 3 is configured for:

- determining a plurality of ratios (optical count ratios),
- providing as input to one or more neural networks NN the plurality of ratios and the temperature value,
- processing the plurality of ratios by means of one or more neural networks NN taking into account a plurality of data from previous measurements of blood parameters made during previous training (laboratory training),
- providing as an output from one or more neural networks NN the value of each parameter of the plurality of blood parameters.

Figure 10:
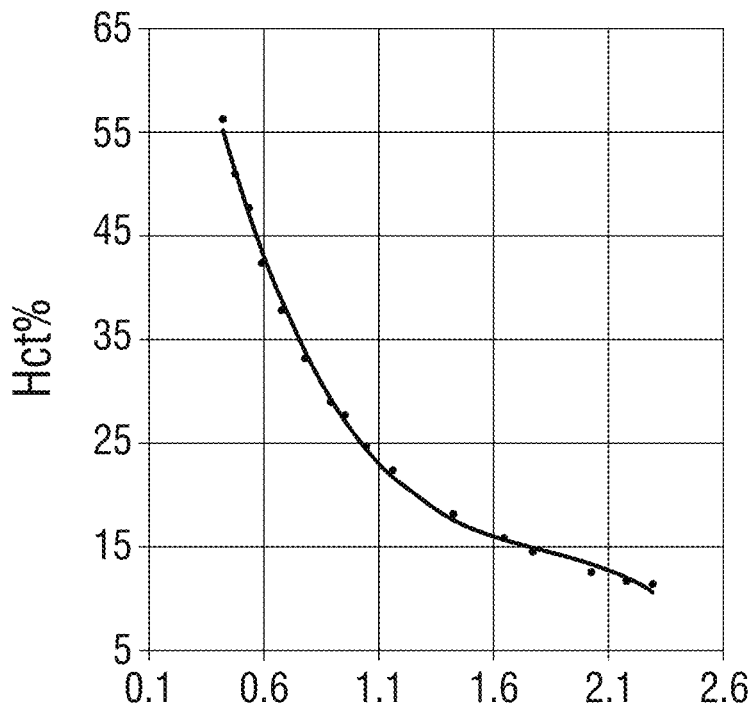
FIG. 10 illustrates a hematocrit calibration curve (Hct %) at a fixed saturation value for calibrating a device according to the invention in the laboratory; the wording on the abscissas indicates the ratio of the optical count detected by the InGaAs (Indium Gallium Arsenide) photodiode due to an excitation at a wavelength of 805 nm (at the numerator) to the ratio of the optical count detected by the indium gallium arsenic photodiode due to an excitation at a wavelength of 1450 nm (at the denominator)
Figure 11:
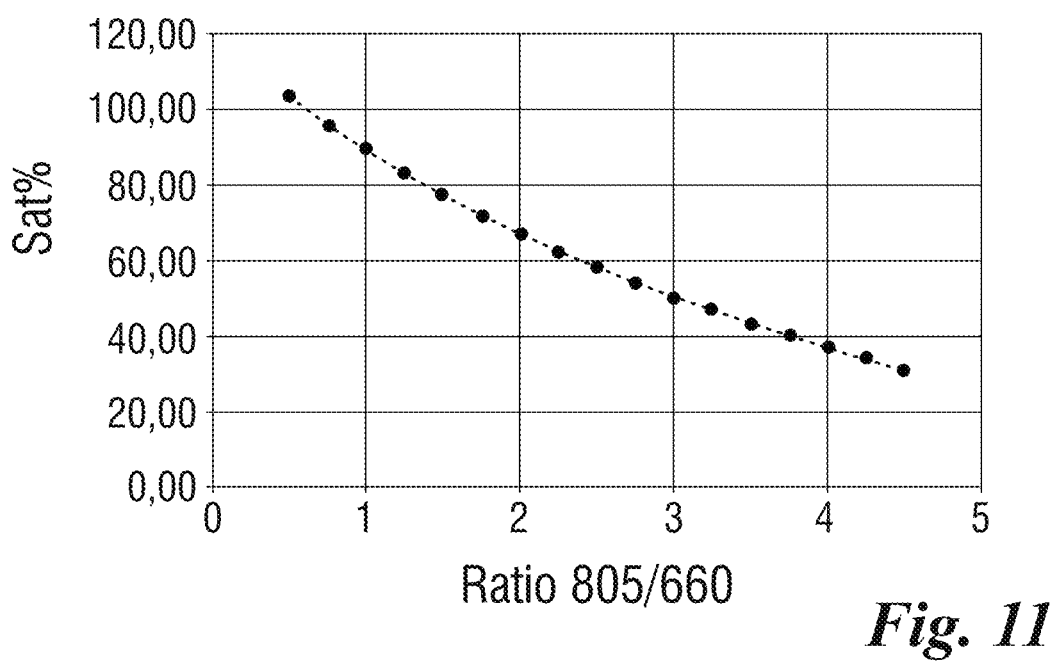
FIG. 11 illustrates a saturation calibration curve (Sat %) at a fixed hematocrit value to calibrate a device in accordance with the invention in the laboratory; the wording on the abscissas indicates the ratio of the optical count detected by the Si (Silicium) photodiode due to an excitation at a wavelength of 805 nm (at the numerator) to the ratio of the optical count detected by the silicon photodiode due to an excitation at a wavelength of 660 nm (at the denominator)

Each ratio is defined between a quantity indicative of the radiation retro-reflected or diffused by the blood due to an excitation at a determined wavelength (count calculated from the radiation received by a photodiode) and a quantity indicative of the radiation retro-reflected or diffused by the blood due to an excitation at another determined wavelength (count calculated from the radiation received by the same photodiode). For example, the x-axis of the graph in FIG. 10 shows "Ratio805InGaAs/1450", which is the ratio of the optical count relative to the radiation read (back-reflected radiation) from the InGaAs photodiode 9 against excitation radiation at 805 nm (numerator of the ratio) and the radiation read (back-reflected radiation) from the same InGaAs photodiode 9 against excitation radiation at 1450 nm. To provide a further example, it is indicated that on the abscissae of the graph in FIG. 11 is "Ratio 805/660" which is the ratio of the optical count relative to the radiation read (back-reflected radiation) from the Si photodiode 8 against excitation radiation at 805 nm (numerator of the ratio) and the radiation read (back-reflected radiation) from the same Si photodiode 8 against excitation radiation at 660 nm.

Basically, the control unit 3 receives as input the actual temperature value of the blood and the analogue electromagnetic and/or light response information from the photodetectors 8, 9, processes it on the basis of the previous training and measures the parameter values. The actual blood temperature value is measured by the temperature sensor 12, which detects the temperature of the blood flowing into the container 25, 25'. With regard to the input of the temperature value, it is indicated that it is useful at least because as the temperature changes, the excitation members have different conditions of emission of electromagnetic radiation and the responses of the blood to the excitation electromagnetic radiation change as a function of temperature.

The control unit 3 is configured to control the plurality of excitation members 4, 5 during an excitation step comprising activating the plurality of excitation members 4, 5 in accordance with a specified time sequence. For example, the control unit 3 may activate the plurality of excitation members 4, 5 in such a manner as to excite the blood, by activating the LED elements one at a time, in accordance with the following time sequence: activating the LED element causing excitation at 660 nm, then activating LED element causing excitation at 805 nm, then activate LED element causing excitation at 1450 nm and finally activating LED element causing excitation at 1550 nm; the other LED elements of 525 nm, 940 nm and 1050 nm are also activated. In essence, it is understood that following a specific time sequence as described above is not essential for the measurement of the plurality of parameters and is therefore not limiting in any way; the control unit 3 can therefore function by exciting the blood in accordance with other excitation sequences.

The control unit 3 is preferably configured to activate, in particular alternately, the first excitation member 4 and the second excitation member 5 so as to excite, in particular alternately, the blood flow at a first wavelength selected from the first plurality of wavelengths (525 nm, 940 nm, optionally 1050 nm) or at the first plurality of wavelengths and at a second wavelength selected from a second plurality of wavelengths (660 nm, 805 nm, 1450 nm) or at the second plurality of wavelengths. Preferably, the control unit 3 is configured to activate, in particular alternately, the first excitation member 4 and the second excitation member 5 so as to excite, in particular alternately, the blood flow at the first plurality of wavelengths and at the second plurality of wavelengths.

The control unit 3 is configured to control at least one excitation member or both excitation members 4, 5 during an excitation step in which the blood flow is excited one wavelength at a time.

In more detail, control unit 3 is configured to activate (switch on) the individual LED elements in a timed manner so that within a given reference time unit (e.g. 1 second) there are dozens of measurements of transmitted optical counts per LED element (per light source). In particular, control unit 3 is configured to activate the individual LED elements in a timed manner in accordance with the previously described timings, so that within 1 second there are 20 measurements of transmitted optical counts for each LED element. As the number of measurements in a given time unit increases, the influence of noise on the measurement has less weight (the acquired measurements can be averaged) and thus the accuracy of the measurement increases as the data used is statistically more reliable.

In essence, the control unit 3 constitutes the member of device 1, 1' equipped with artificial intelligence (on the basis of the machine learning described below) and is configured to detect the value of each parameter that the artificial intelligence deems corresponding, on the basis of the plurality of data from previous measurements, to the previously determined ratios.

In particular, control unit 3 includes artificial intelligence information, e.g. one or more matrices that can be used by said one or more neural networks, encoded in its firmware and enabling the calculation of a plurality of parameters by means of one or more neural networks NN and by means of a given calculation model.

In addition to the information encoded in the firmware, the control unit 3 is configured to provide as input to the one or more neural networks a reference value of a first parameter to be measured (oxygen saturation) and a reference value of a second parameter to be measured (hematocrit). These reference values are acquired and stored in a memory (e.g. an EEPROM memory) of the device during a calibration step prior to use of the device 1, 1'; the memory may be part of the control unit 3. Such a calibration prior to use of the device 1, 1' may be performed by the manufacturer of the device 1, 1', for example in a laboratory; in any case, it is not performed by the end user.

The information, in particular the artificial intelligence information, encoded in the firmware is the same for each device 1, 1' that is produced, whereas the aforementioned information stored in the memory may vary between devices 1, 1' as it takes into account, by means of the calibration that is carried out in the laboratory, the variability of each individual device 1, 1' which may be linked to the following factors: hardware, variability of the components and their specific, even infinitesimal, geometric position within the box body of the device.

Control unit 3 can also be configured to take into account a blood flow-related value, in particular the volumetric blood flow rate, when measuring oxygen saturation and/or hematocrit. Control unit 3 can perform this by correcting the measured values of oxygen saturation and/or hematocrit depending on the blood flow as described below.

In terms of components, the control unit 3 may comprise at least an Microprocessor MP and an analogue digital converter (ADC). The Microprocessor MP can determine and supervise the performance of the above operations and the ADC performs the operation of converting the analogue information into digital data. The artificial intelligence information is encoded in the firmware of the Microprocessor MP. The control unit 3 may include the previously mentioned memory, for example an EEPROM memory.

The control unit 3 may also include an analogue 'AFE' front-end (AFE chip), i.e. a system that integrates the analogue technology required to achieve optimal interfacing to the analogue/digital converter. This interfacing fundamentally concerns the adaptation of the analogue signal captured by the sensors (photodetectors) to the functional specifications of the analogue/digital converter with regard to amplitude dynamics (amplification) and frequency bandwidth (anti-aliasing filtering), i.e. with regard to the principles of sampling analogue signals. In fact, the analogue front-end performs a complex of analogue signal processing, generically referred to as 'conditioning', most of which is strictly dependent on the application and the nature of the sensors (photodetectors).

The control unit 3 may further comprise at least one printed circuit board assembly PCB1. In essence, the printed circuit board assembly PCB1 is a board populated with, i.e. on which are arranged, certain electronic components enabling the assembly to perform the function or functions for which it is intended. As illustrated in the enclosed figures, control unit 3 may comprise a first printed circuit board PCB1 for the Microprocessor MP and a second printed circuit board PCB2 for the analogue front-end. As illustrated in FIG. 7, constraining elements 2e, in particular threaded elements, may be provided to secure the printed circuit assembly PCB1, the excitation members 4, 5 and the electromagnetic radiation detection members 8,9.

The values of oxygen saturation and hematocrit are calculated by the artificial intelligence of device 1, 1' at substantially the same instant; the measurement of these parameters is therefore substantially instantaneous. Furthermore, the output parameters (Hematocrit, Saturation, Hemoglobin) are provided by the device 1, 1', via the control unit 3, at the same instant; the temperature data, measured without the aid of artificial intelligence, is also synchronised with the other parameters and is output together. Thus, the end user of the device 1, 1' has all the parameters measured by the device 1, 1' available at the same time and, in particular, can display them on a user interface, such as a display means 91, operably connected or connectable to the device 1, 1'. The parameters can be made available at a certain cadence (e.g. every second, every 5 seconds, every 10 seconds) or continuously and, additionally or alternatively, on demand (e.g. at the request of a medical machine 90', 90').

In the second embodiment of the device 1', according to which the device can be associated with a tube 25', control unit 1 is configured to perform the following operations:
  detecting a tube 25' type,
  preparing for measurement based on the type of tube 25' detected.

Among the characteristics in which tubes 25' may differ, it is important to note their colour or shade as it can alter the blood's response to electromagnetic excitation. tubes 25' are typically plasticised polyvinyl chloride (PVC), or at least are based on it, and are not perfectly transparent. Furthermore, the sterilisation to which the tube 25' may be subjected prior to its use may also result in a change in the colour or shade of the tube 25'. It should be borne in mind that if the actual colour or shade of the tube 25' on which measurements are made is not appropriately taken into account, the blood response received by the electromagnetic radiation detecting members would not be correct (e.g. because the device 1, 1' might expect a transparent container when in fact the tube is not, thus modifying the electromagnetic response "recorded" by the electromagnetic radiation detecting members) and therefore the measurement of the desired parameters would not be reliable.

The detection of the tube 25' type then involves the detection of the colour or shade of the tube 25'; the control unit 3 then prepares itself, on the basis of the colour or shade of the tube 25' detected, for measurement, e.g. by adapting the mode of measurement of one or more parameters to the container or tube 25' type detected.

The detection of the colour or shade of the tube 25' is carried out before the blood is excited, in particular before the blood flows into the tube 25'. When the colour or shade of tube 25' is detected, saline solution or other fluid other than blood preferably flows into the tube 25'.

The control unit 3 is configured to perform the operation of preparing for measurement on the basis of the colour or shade of tube 25' detected by selection of a given matrix from a plurality of matrices usable by the neural network NN; each matrix corresponds to a given colour or shade of tube 25'. This selection operation may be performed by consulting the memory of the device 1, 1' in which information relating to the plurality of matrices is stored.

The technical features disclosed herein in relation to functions of the device 1, 1' or portions/components/elements thereof, in particular to operations of the control unit 3, are applicable in the context of corresponding uses of the device or method steps described below and may therefore be used to specify such uses and method in the appended claims.

Machine Learning Set-Up Based on One or More Neural Networks

Figure 9:
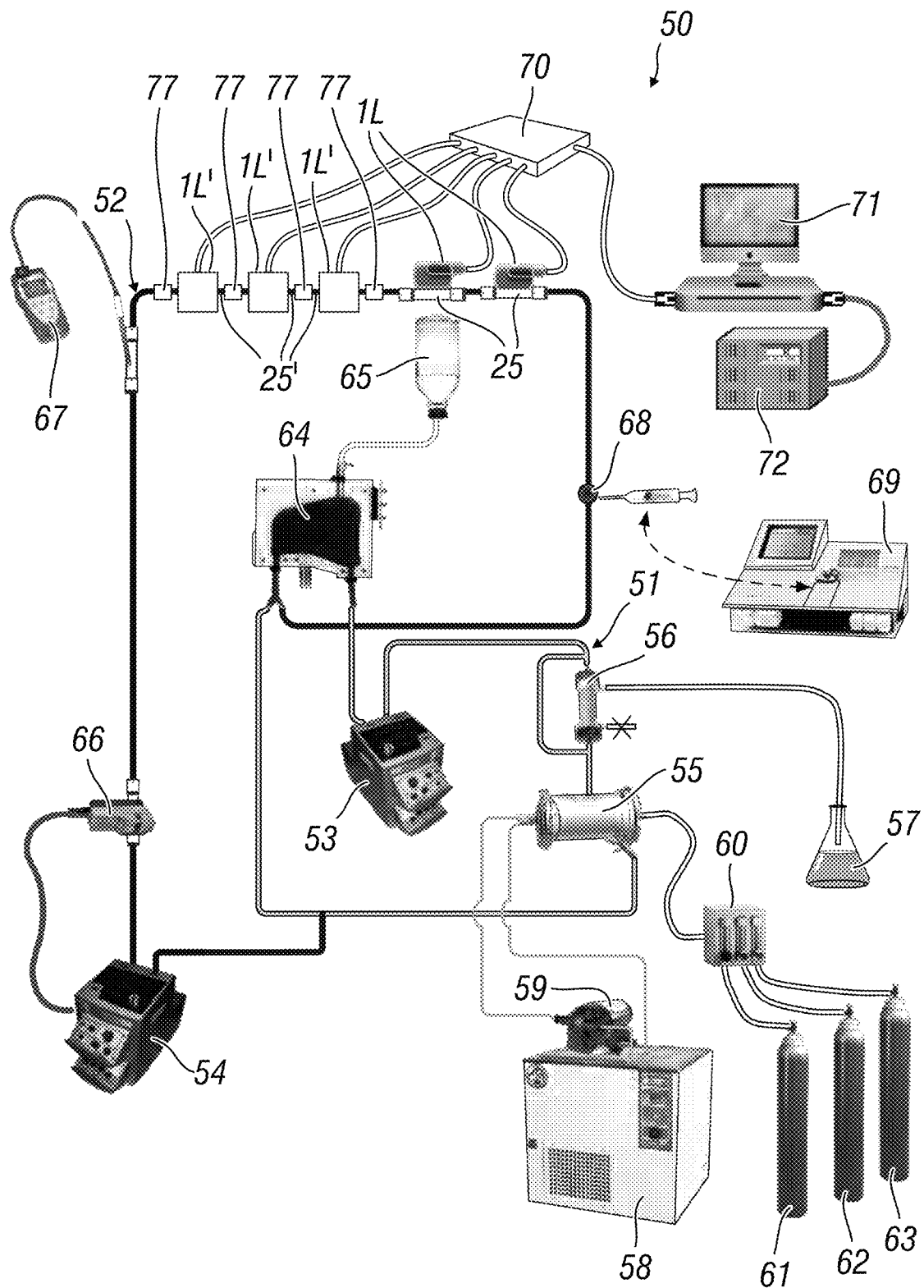
FIG. 9 illustrates a laboratory set-up to enable automatic learning by devices according to the invention.

The learning takes place by extensive ex-vivo laboratory testing, i.e. conducted using extra-corporeal blood prepared and circulated in a set-up 50 in which the conditions of the blood and the environment are changed to simulate substantially all possible conditions to which the device 1 according to the invention may be subjected in clinical use (see FIG. 9). The conditions that are simulated are blood temperature, blood flow rate, ambient temperature, blood oxygen saturation and blood hematocrit. The set-up 50 by which the devices are tested and trained to determine an automatic learning model in the laboratory is described below. In the learning tests performed, the environmental conditions were not varied; measurements were therefore acquired at room temperature. However it should be noted that, in general, it is possible to vary the ambient temperature; this would entail the use of the set-up 50 in a environmental chamber.

The set-up 50 is shown in FIG. 9 and comprises two circuits along which extra-corporeal blood circulates. In more detail, there is a blood preparation circuit 51 and a main blood circuit 52 in which blood, suitably prepared by means of the blood preparation circuit 51, is circulated to perform the parameter measurements. The circuits 51, 52 are depicted differentially in FIG. 9, by means of respective and different lines. The main blood circuit 52 is illustrated predominantly in the upper part of FIG. 9 (it extends, on the left in FIG. 9, to the lower part of the figure), while the blood preparation circuit 51 is illustrated in the lower part of FIG. 9. In the blood preparation circuit 51 and the main blood circuit 52 the blood is circulated by a respective handling member 53, 54; in particular, for this purpose the illustrated set-up provides a main centrifugal pump 54 for the main blood circuit 52 and a secondary centrifugal pump 53 for the blood preparation circuit 51.

The blood preparation circuit 51 allows for the preparation of blood under the desired conditions. For this purpose, the set-up includes a blood oxygenator 55 and a plasma filter 56 arranged along the blood preparation circuit 51.

The plasma filter 56 is the component whose function is to extract plasma from the blood so that the blood can be 'concentrated' to increase the hematocrit value. Plasma filter 56 is connected to an extracted plasma discharge container 57, into which the plasma removed by plasma filter 56 is poured. The removal of plasma occurs due to the pressure gradient established between the blood preparation circuit 51 and the extracted plasma discharge container 57; to interrupt the removal, the line connecting the plasma filter 56 to the extracted plasma discharge container 57 is closed.

Regarding the blood oxygenator 55, it is the component of the set-up 50 having, in the blood preparation circuit 51, functions equivalent to those of human lungs; it is configured to oxygenate blood, remove carbon dioxide and also heat or cool blood as described below. For this purpose, the blood oxygenator 55 includes a heat exchanger and is connected with a thermostatic bath 58. The set-up 50 further includes a water pump 59 configured to circulate water between the thermostatic bath 58 and the blood oxygenator 55. The thermostatic bath 58 is configured to heat or cool the water, which by means of the water pump 59 is circulated in the heat exchanger integrated in the blood oxygenator 55; as a result, it cools or heats the blood to the desired temperatures. In order to change the saturation conditions of the blood, and in particular the oxygen saturation conditions of the blood, the blood oxygenator 55 is connected to a gas mixer 60, which is in turn connected upstream with an oxygen tank 61, a nitrogen tank 62 and a carbon dioxide tank 63. The gas mixer 60 is configured to mix in varying proportions the gases from the three tanks 61, 62, 63 just described. As illustrated in FIG. 9, the tanks may be in the form of cylinders 61, 62, 63 configured to send the respective gas to the gas mixer 60.

The blood preparation circuit 51 and the main blood circuit 52 share a common element, consisting of a blood container 64, which is illustrated in FIG. 9 as a blood bag. The blood container 64 acts as a reservoir from which blood is drawn by the secondary centrifugal pump 53 and, since the blood preparation circuit is a closed circuit, it returns to it suitably prepared. The blood container 64 is connected to an isotonic solution source 65, which is configured to provide isotonic solution. As the isotonic solution is devoid of red blood cells, its supply to the blood container 64 allows the blood contained therein to be diluted. The isotonic solution, otherwise referred to as saline solution, enters the main blood circuit 52 by gravity and performs the opposite action to that performed by the plasma filter 56. The blood container 64 allows the main blood circuit 52 to be fed, by means of the main centrifugal pump 54, with suitably prepared blood from the blood preparation circuit 51 just described.

The set-up 50 also provides, along the main blood circuit 52, a plurality of devices 1L, 1L' (wherein "L" stands for learning, indicating that these devices are subject to automatic learning) associated with respective containers 25, 25' of the type described above. In more detail, the devices 1L are of the type corresponding to the first embodiment (and are associated with respective cuvettes 25) while the devices 1L' are of the type corresponding to the second embodiment (and are associated with tubes 25'), with the difference, with respect to the devices 1, 1', that the devices 1L, 1L' are subject to machine learning in order to develop the artificial intelligence (calculation method, firmware, related logic and code) that will then be implemented in the devices 1, 1', whereas the devices 1, 1' are already equipped with the artificial intelligence and only need a brief calibration in the laboratory before they can be delivered and used. The containers associated with the devices 1L, 1L' are respectively cuvettes 25 and tube pieces 25' arranged along the blood main circuit 52. The tube pieces 25' have different formulations with each other (thus different colourations typically) and are connected by means of connecting elements 77 (see FIG. 9); the colouration and/or shading of the individual tube pieces 25' depends on the chemical formulation of the tube material and/or the tube sterilisation process. A plurality of devices 1L' connected to tube portions of the same type, i.e. of the same formulation and of the same colour or shade, may be provided; in such a case, a single tube of the same colour or shade may be provided instead of individual tube pieces. Providing that the devices 1L' learn to recognise and distinguish different types, colours and/or shades of tubes is advantageous in order to provide an accurate measurement of the parameters; the artificial intelligence derived from machine learning provides the device 1' with the necessary information to prepare it to recognise different types, colours and/or shades of tubes and to adjust the measurement accordingly. The cuvettes 25 and tube pieces 25' coupled to the devices 1L, 1L' respectively are of disposable type. The set-up 50 in FIG. 9 allows the probes to learn the behaviour of different tube types. For the learning trials, pieces of tube 25' of the same colour can be provided at the same time (i.e. in the same learning session or epoch) to collect more statistically valid data; subsequently, the type of tube is changed (replacing the pieces of tube 25' with other pieces of tube of a different colour) and more data are collected, and so on to have a large case history for training the neural network.

The devices 1L, 1L' provided by set-up 50 are therefore opto-electronic probes configured to excite the blood and to detect the related electromagnetic and/or light response; their opto-electronic excitation unit (excitation members) and their electromagnetic and/or light response detection components (electromagnetic radiation detection members) are similar to those previously described with reference to the respective embodiments of the devices 1, 1'. In essence, the devices 1L, 1L' of the set-up are of the type previously described, except for the fact that they lack the algorithm enabling autonomous measurement of the blood parameter in clinical use, as this algorithm is precisely being developed through the training described herein to which the devices 1L, 1L' are subjected. In more detail, devices 1L, 1L' and devices 1, 1' differ in their calibration coefficients, which are described below. Following the preparation, by means of learning, of said devices 1L, 1L', carried out precisely by learning in the laboratory, the devices 1L, 1L' will be configured to calculate the value of the parameters using the appropriately trained neural network(s) for all the operating conditions that are expected to occur during clinical use of the device 1, 1'. It is reiterated that this learning/calibration takes place in the laboratory, i.e. prior to the clinical use of device 1, 1'. As illustrated in FIG. 9, the cuvettes and respective devices 1L may be in a number of two, while the devices 1L' may be in a number of three; it is understood that a plurality of devices 1L and respective cuvettes in a number greater than two and/or devices 1L' in a number of two or greater than three may be provided. In an embodiment, at least five devices 1L and at least five devices 1L' may be provided. As the number of devices 1L, 1L' increases, the number of "raw" data collected increases and greater variability between devices is included.

The devices 1L, 1L' during learning 'interrogate' the blood by emission of electromagnetic radiation at different wavelengths and detect the response in electromagnetic radiation by deriving, as described below, calibration curves, in particular at least one calibration curve of hematocrit at fixed oxygen saturation value and at least one calibration curve of oxygen saturation at fixed hematocrit value.

The set-up 50 also includes, along the main blood circuit 52, a blood flow meter 66 and a temperature detector 67; the latter serves as a temperature verification and reference instrument.

The blood flow meter 66 is configured to measure the blood flow rate in the main blood circuit 52. The blood flow meter 66 can measure the blood flow rate downstream of the main centrifugal pump 54. In FIG. 9, the blood flow meter 66 is shown as connected to the main centrifugal pump 54.

The temperature detector 67 is configured to measure the temperature of the blood, preferably in the vicinity of the containers coupled to the respective devices. In FIG. 9, the temperature detector 67 is illustrated in the form of a digital thermometer having a temperature sensor immersed in the blood and arranged upstream of and in proximity to the containers coupled to the devices 1L, 1L'.

The main blood circuit 52 further comprises a blood sampling point 68 and a reference blood analyser 69. The blood sampling point 68 is a point in the circuit at which an extra-corporeal blood sample is taken; the sample taken is analysed by the reference blood analyser 69, which is the reference instrument to which the "raw" measurements of the parameter (and the related "raw" data) obtained from the plurality of devices 1L, 1L' are referred. The reference blood analyser 69 is a clinically accepted reference instrument and therefore provides the measurement of the parameter with the necessary accuracy. In essence, the reference blood analyser 69 provides a reference value of the parameter under the specific conditions (actual blood temperature and, for example, blood oxygenation) under which the measurement was made. In the tests performed, the blood reference analyser 69 measures at least the oxygen saturation value of the blood, the hemoglobin concentration and the hematocrit value of the blood. The blood reference analyser shown in FIG. 9 is a laboratory blood chemistry analyser 69.

Using the set-up 50 of FIG. 9, the previously indicated conditions are then varied and, for each variation, the electromagnetic radiation responses resulting from the excitation of the blood are acquired. The ratios between optical counts are thus acquired and calibration curves are generated; the curves thus acquired are digitalised by means of the components that are on board the device 1L, 1L'.

In this way, the analogue information of electromagnetic and/or light response of the blood for a given change in a condition is transformed into digital data that can be processed. The value of the parameter corresponding to the changed condition, the analogue information and the corresponding digital data are associated with the value of the parameter (in the tests performed, oxygen saturation and hematocrit) measured by the reference blood analyser. By extensively simulating each possible condition that may occur in clinical use, thousands of associated parameter/digitalised curve data are obtained for each of the conditions set in the laboratory, ranging from all those for which you want the device 1, 1' to measure parameters (oxygen saturation and hematocrit).

The set-up further comprises a data collector 70 and a data processor 71. The data collector 70 is connected to the plurality of devices 1L, 1L' in order to collect data from the devices 1L, 1L'; the data collected is digital data relating to the electromagnetic and/or light response of the blood. As illustrated in FIG. 9, in order to collect the data the data collector 70 may have a plurality of inputs corresponding in number to the devices 1L, 1L' of the set-up 50 and at least one output for connection to the computer 71. The data collector 70 is essentially an electronic instrumentation; the data collector used in the tests, illustrated in FIG. 9, is a multiplexer 70. After collecting the data, the data collector 70 transfers it to the processor, which is illustrated in FIG. 9 as a personal computer 71. The computer 71 collects "raw" data from the devices 1L, 1L' for all the operating conditions intended to be tested; this "raw" data constitutes a data set used for training the neural network.

The set-up 50 may further provide for an external archive 72, connected to the computer 71 and configured to store data received from the computer 71. In essence, the external archive is an electronic archive 72, which may be remote, for storing data.

Having described the set-up 50 enabling training, the machine learning method based on neural networks NN is now described.

Machine Learning Method Based on One or More Neural Networks

As mentioned by means of the set-up in FIG. 9, it is possible to vary the conditions of temperature, oxygen saturation and blood hematocrit in discrete steps in all the intended ranges of measurement (13-55% for blood hematocrit, 35-99.9% for blood oxygen saturation and 9-42° C. for blood temperature) and for each of the multiple combinations of these parameters. The process of learning and designing the device for the correct measurement of Sat % and Hct % is accomplished by performing the following steps.

1) The setting of the gains, intensity of the individual LED elements, i.e. maximisation of the optical counts for each of the individual LED elements in the conditions at the extremes of the measuring range of Hct % and Sat % is carried out. The gain is the ability of the photodiode to convert the light signal into an electrical current signal, while the optical counts are an indicative measure of the signal transmitted through the tube and detected by the photodiode. The maximum count value is approximately 4000, beyond this value the signal is saturated, and therefore no longer indicative for measurement; it is therefore necessary, under extreme measurement conditions (i.e. for the measurement of parameters at the ends of their measuring ranges), to set the counts so as not to exceed this maximum threshold.

2) The calibration curve of the Hct % is constructed by means of a "best fitting" technique with a 4th order curve of the ratio of the values of the optical counts of the electromagnetic radiation read by the InGaAs photodiode 9 against excitation at 805 nm and of the electromagnetic radiation read by the same photodiode 9 against excitation at 1450 nm with respect to those obtained by the reference instrument. The oxygen saturation value of the blood Sat % is kept fixed at 80%, the blood temperature at 37° C. and the hematocrit value is increased in steps of 3 percentage points in the range 12-55 Hct % (see FIG. 10; ratio=Counts805/Counts1450). Each point indicated on the graph in FIG. 10 corresponds to a measurement taken.

3) We then proceed to construct the calibration curve of the oxygen saturation of the blood Sat %, by means of a "best fitting" technique with a 3rd order curve of the ratio of the values of the optical counts of the electromagnetic radiation read by the silicon photodiode 8 against excitation at 805 nm and of the electromagnetic radiation read by the same photodiode 8 against excitation at 660 nm. The blood hematocrit value Hct % is kept fixed at 15%, blood temperature at 37° C., increasing steps of Sat % by 5 points in the range 35%-98% (see FIG. 11; ratio=Counts805/Counts660). Each point indicated on the graph in FIG. 11 corresponds to a measurement taken.

4) We then proceed to construct the temperature calibration curve (linear relationship between fluid temperature detected by the device and that of the reference instrument with data acquisition at 24±2° C. ambient temperature).

5) In this step, artificial intelligence, using a neural network NN of the type described below, is used to create a weight matrix for the accurate calculation of Sat % and Hct % including their interdependencies. This step requires the acquisition of a data set for each tube or cuvette with which the devices are to operate. The data set is acquired by setting the Hct % and blood temperature and scanning the Sat % values for each established Hct %; the scan is performed by varying the blood conditions to obtain Sat % values in its entire range and the procedure is repeated for each Hct % value in its entire range. According to the methodology used, after setting a certain temperature of the blood, a certain value of Hct % was kept fixed and a scan was made over the entire measuring range of the Sat %; then, at the same temperature of the blood, the value of Hct % was changed and a scan was made again of the Sat % and so on so as to cover the entire measuring range of the Hct %. Next, another blood temperature was set and the above two scans of Hct % and Sat % were repeated. The aim is to cover essentially all possible values of Sat % and Hct % in the desired temperature range, i.e. to cover all values of the parameters of interest blood temperature, Hct % and Sat % in their respective ranges. We have just described the methodology that was used to achieve this goal, which proved to be advantageous; it is understood that other methodologies could achieve the same goal in other ways (e.g. by setting the temperature following a value of Hct % or otherwise using another sequence of setting and variation of the parameters blood temperature, Hct % and Sat %).

6) In this step, artificial intelligence is used to calculate the dependency of Hct % on Sat %; this step can be performed by using the same neural network NN used for step 5) or another neural network (second neural network) with essentially the same structure.

7) In this step, artificial intelligence is used to calculate the dependence of Hct % on blood temperature this step can be performed by using the same neural network as in step 5) or another neural network (third neural network) with essentially the same structure.

Preferably, only one neural network NN is used in the learning. If greater accuracy is desired, two more neural networks, i.e. the second and third neural networks, can be incorporated to improve the results from the output of the first neural network (neural network of step 5).

Each neural network preferably has the following structure and calculation method.

Figure 12:
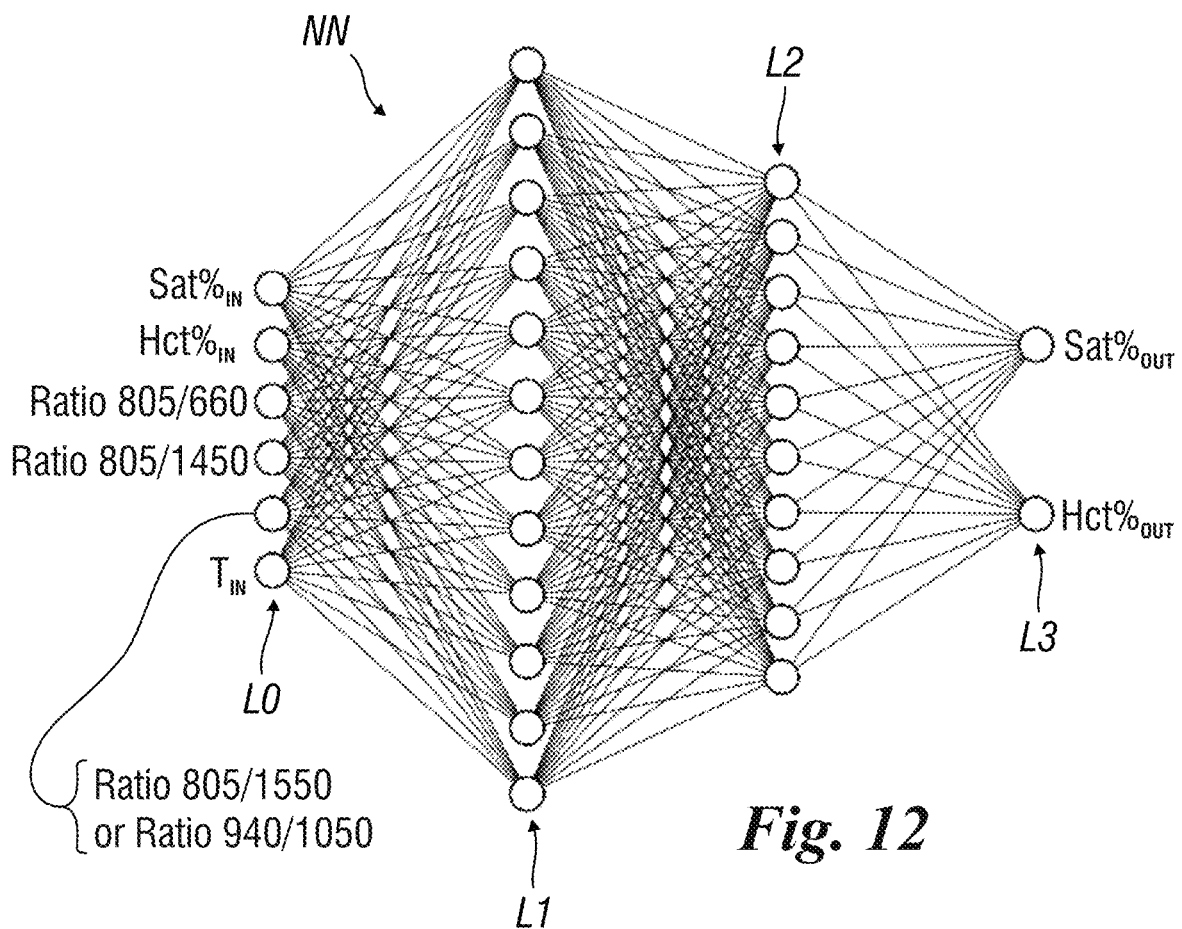
FIG. 12 illustrates by way of example the structure of the multilayer perceptron-type neural network, which is one possible structure of one or more neural networks that may be implemented in the device in accordance with the present invention.

In the tests performed, a multilayer perceptron-type neural network NN (MLP or Multi Layer Perceptron) was chosen, which is illustrated in FIG. 12. The multilayer perceptron-type neural network NN is an artificial neural network model that maps input data sets into an appropriate output data set. Furthermore, such a neural network NN is of feedforward type, i.e. it is an artificial neural network in which connections between nodes do not form a loop. It is understood that, depending on the machine learning method one wishes to implement, different types of machine-learning neural network can be chosen; the type of neural network chosen is described below, with reference to the application tested, which involved the measurement of oxygen saturation and hematocrit parameters directly by means of artificial intelligence. Clearly, the following is applicable, mutatis mutandis, to the measurement of one or more other blood parameters.

The neural network NN of FIG. 12 presents an input or input layer L0 with six neurons, a first layer L1 completely connected by twelve neurons, a second layer L2 completely connected by ten neurons and a third layer L3 completely connected by two neurons. The two neurons of this last layer L3, which constitutes the output layer or output, correspond to the output values of the neural network, namely: the Sat % value and the Hct % value. Notwithstanding the number of neurons of the output layer L3, the other layers L0, L1, L2 may present a number of neurons and/or a number of layers different from that described here, depending on the specific optimisation carried out for the chosen neural network model. The number of neurons for each layer may be partially constrained by the computational capacity of the microprocessor MP of the control unit 3 of the device 1L, 1L'. All the neurons in the network are sigmoidal in activation; the activation of a neuron corresponds to the moment when the neuron activates and operates its information transfer function (illustrated in FIG. 14 and hereafter referred to as sigmoid), which enables the transmission of the incoming stimulus information.

The input data to the neural network NN (input data) is described below; see FIG. 12. Two of the six neurons of the input layer L0 correspond to the values of Sat % and Hct % (respectively Sat % IN and Hct % IN in FIG. 12) measured by the device 1L, 1L', while three of the six neurons correspond to the values of the ratios 805/660, 805/1450, 805/1550 or alternatively 940/1050; the 805/1550 ratio is used to improve the measurement accuracy of Hct % while the 940/1050 ratio is used because at a wavelength of 1050 nm both have good dynamics of variation throughout the measurement range of Sat %. The other neuron in layer L0 corresponds to the blood temperature value (TIN in FIG. 12) detected by temperature detector 67.

The input parameters are scaled to be normalised in amplitude in order to prevent very large values from weighing more heavily in the neural network than small ones, and also to allow more efficient training of the neural network. Basically, based on the collected learning set, the minimum and maximum values of each parameter input to the network are calculated and normalised before they are passed to the network and denormalised afterwards to obtain the output data. The values have to be rescaled before being passed to the network in this way: normalised value=(collected value-minimum value)/(maximum value-minimum value). Similarly, the value output from the network has to be re-scaled to obtain the actual value in this way: denormalised value=value*(maximum value-minimum value)+minimum value.

The neural network NN is then able, on the basis of the input of the above-mentioned data, to calculate the Sat % and Hct % value of the blood flowing into the container (output data). This calculation, which makes the measurement made by the device possible, in the neural network chosen and tested is carried out as follows.

Figure 13:
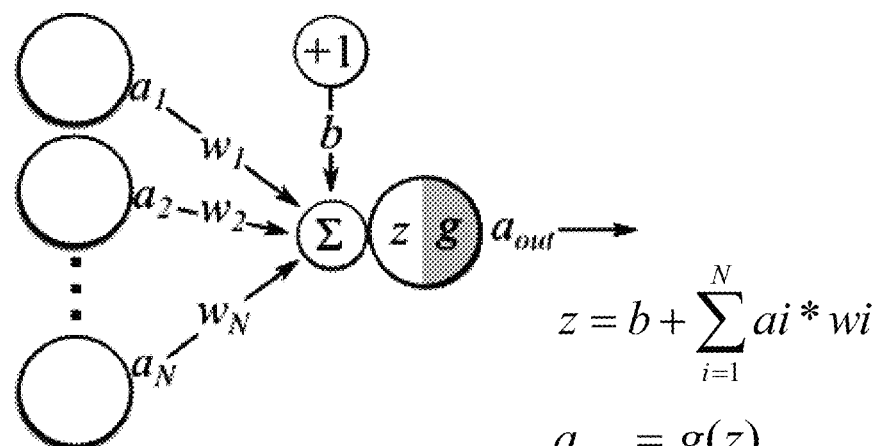
FIG. 13 illustrates a possible calculation method that can be implemented by the neural network in FIG. 12 to measure the values of the blood parameters output by the neural network.

The calculation method used is shown in FIG. 13 and involves the following formulas, where the symbol * indicates the scalar product:

$$z = b + \sum_{i=1}^{N} ai * wi \quad \text{(formula 1)}$$

$$a_{out} = g(z) \quad \text{(formula 2)}$$

In formula 1, it should also be specified that:
$w_i$=weight$_i$
$b_i$=bias$_i$
"wi" and "bi" are matrices of weights and biases respectively; weights and biases are the calibration coefficients.

By providing matrices, the calculation model is a mathematical matrix model.

As far as formula 2 is concerned, it is specified that $a_{out}$ is the output of each neuron, thus also those of the inner layers L1, L2.

In more detail:
for the first layer L1:
a1=x_input*w1+b1
z1=sigmoid(a1)
for the second L2 layer:
a2=z1*w2+b2
z2=sigmoid(a2)
for the third layer L3:
a3=z2*w3+b3
z3=sigmoid(a3)
output=z3

As there are two neurons in the output layer L3, one of them has Sat % as its output, while the other has Hct % as its output, i.e. the desired output parameters related to the blood circulating in the container to which the device is joined.

Figure 14:
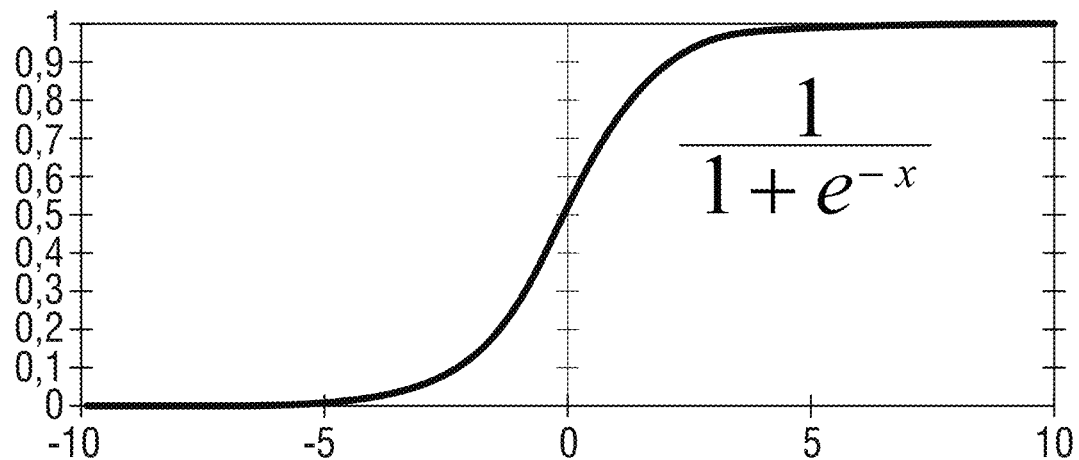
FIG. 14 illustrates the activation function of the neurons in the neural network of FIG. 12.

It should also be noted that:
"i" ranges from 1 to N,
"N" is the number of nodes (neurons) for each layer of the neural network,
"x_input" is the vector of input values/parameters (vector containing the parameters related to optical counts and blood temperature),
"a", "b", "w", derive from the learning phase,
"g(z)" is the neuron's activation function and is illustrated in FIG. 14.

The learning process, using example measurements, optimises the values of the weights and bias matrices and derives a matrix of weights and bias for each layer, so w1 and b1 are the matrices of weights and bias of the first layer L1, w2 and b2 those of the second layer L2 and w3 and b3 those of the third layer L3. Optimising, i.e. finding values of weights and biases that are 'optimal', means finding those values of weights and biases that minimise a cost function, which represents the error between the actual measurement and the prediction made of the network.

The algorithm implemented in device 1, 1' executes the instructions shown in FIG. 13. Several thousand training epochs were run (1 epoch corresponds to a complete cycle of all examples) with an average batch size of 4 examples per batch. In the tests performed, learning was carried out for 4*105 epochs and with an adaptive learning rate starting from a value of 0.001 to avoid over-fitting. It should be noted that the learning rate is one of several parameters that is set during the learning phase of the neural network; it modifies the optimizer step. The optimizer known as 'Adam' was used, which is a derivation of the gradient method. In neural network terminology:

an epoch=a forward pass and a backward pass of all training examples. An epoch describes the number of times the algorithm sees the entire dataset. Thus, each time the algorithm has seen all the samples in the dataset, an epoch has been completed.

batch size=the number of training examples in a forward/backward passage. The larger the batch size, the more memory space is required.

number of iterations=number of passages, each passage using the number [batch size] of examples. One passage=one forward passage+one backward passage (the forward passage and the backward passage as two different passages are not counted).

For non-specifically detailed aspects of machine learning, please refer to the literature on neural network theory.

For each link in the network, there is a function, transposed into C language code in the Microprocessor MP, called a sigmoid, i.e. a mathematical function (sub-layer) that connects the neurons. The inputs of each neuron in the network are matricially multiplied with the network parameters, the result of which is passed to the sigmoid function using the above formulas. The result of the sigmoid function represents the intermediate output of each layer or the input to the neurons of the next layer.

During learning, a non-linear cost function (Mean Absolute Error) was chosen, modified to quadratic weighting the examples at low Sat % and Hct % (which are subject to a higher percentage error).

The final output of the neural network NN model is represented by a set of parameters, i.e. matrices of weights and biases $w_i$ and $b_i$. In essence, the neural network model learns, through extensive laboratory tests and measurements, which are the best values of the weights and bias matrices $w_i$ and $b_i$ capable of providing the two values of the blood parameters (Sat % and Hct %) as output against the input vector x_input. The mathematical model of the multilayer perceptron network was then implemented in C code in the Microprocessor MP of device 1, 1'.

To summarise, the procedure is as follows. The neural network model is chosen, i.e. the number of layers, the number of neurons in each layer and the activation function of the neurons are defined.

The procedure goes on with the learning process, using exemplary measurements and optimising the values of the weights and bias matrices $w_i$ and $b_i$. There is a matrix of weights and biases $w_i$ and $b_i$ for each layer, so w1 and b1 are the matrices of weights and biases of the first layer, w2 and b2 are the matrices of weights and biases of the second layer and w3 and b3 are the matrices of weights and biases of the third layer (and so on if further layers are provided). By 'optimise' or 'optimal values' we mean to find those values of weights and biases that minimise a cost function representing the error between the actual measurement and the predictive measurement made by the network. After defining x_input, i.e. the vector containing the parameters from the ratios of the optical counts or directly from the optical counts and the blood temperature, the algorithm implemented in the device performs the operations illustrated in FIG. 13 and summarised above.

The calculation method that has been developed, which is the result of machine learning, is essentially an algorithm that is encoded and implemented in the Microprocessor MP of the device to perform the measurement of blood parameters. The calculation method and thus the algorithm are preferably encoded in program code, in particular in C code, to be executed by the microprocessor during clinical use of the device 1, 1'. Implementing the calculation method and the algorithm in the Microprocessor MP of the device 1, 1' makes the device 1, 1' according to the invention independent in clinical use; all the calculations necessary to measure the blood parameter are performed by the control unit on board the device and can be transmitted by serial cable to the medical machine with which it interfaces, which takes only the "finished data" of the measurement (i.e. the data ready for use by medical personnel) without performing calculations.

The device 1, 1' has inside it all the information to perform the parameter measurements. The firmware code is written in such a way that for each of the two electromagnetic wavelength ratios that the device 1, 1' calculates by acquiring the relative intensities, together with the blood temperature value also measured by the device, become the model's input parameters. Each device 1, 1' is then programmed to have the matrices containing the weights and biases stored (in the EEPROM memory) while the algorithm based on the calculation method is written (encoded) in the firmware.

It has been verified that the neural model of devices trained in this manner has a measurement/estimation capability of the output values of Sat % with an accuracy of ±6% over the entire measurement range and for all conditions and of the output values of Hct % with an accuracy of ±3% over the entire measurement range and for all operating conditions; this accuracy is achieved using the matrices containing the weights and biases (derived from the neural network model based on what the device learned during the learning phase).

More Details on the Neural Networks

The neural network(s) are constructed with the following assumptions. Three neural networks are described below; the device is referred to as 'probe'. Each network has a number of neurons in the input layer L0 equal to the number of input values and a number of neurons in the output layer L3 equal to the number of output values.

| 1st Neural Network | Data matrix to determine neural network coefficients | Neural Network Output |
|---|---|---|
| Calculation of Sat % and Hct % throughout the range (including their inter-dependencies) | Inputs: Sat % probe Hct % probe Optical count ratio 805/660 Optical Count Ratio 805/1450 Tfluid (Blood temperature) Optical count ratio 940/1050 or optical count ratio 805/1550. In which: Sat % probe and Hct % probe are those measured by the probe from the two initial calibration curves; in this regard, see steps 2) and 3) of the neural network-based machine learning method described above Optical counts/ratios at different Sat % values (10-15 Sat % values at different Hct %), Hct % (15, 20, 30, 40, 50%) and Fluid Temperature (10° C., 15° C., 24° C., 32° C., 37° C., 41° C.) Target values to minimise error (i.e. values measured by the reference instrument) Sat % measured by reference blood analyser 69 Hct % measured by reference blood analyser 69 | Matrix of coefficients/ weights replacing calibration curves for final accurate Hct % and Sat % in the ranges 13-55 of Hct % and 40-99 of Sat % |

Below are the reference photodiodes for reading optical counts:
 optical counts ratio 805/660: Si photodiode,
 optical counts ratio 805/1450: InGaAs photodiode,
 optical counts ratio 940/1050: Si photodiode,
 660 optical counts: Si photodiode,
 optical counts of the 805: Si photodiode,
 805 optical counts: InGaAs photodiode,
 optical counts from 1450: InGaAs photodiode,
 optical counts from 1550: InGaAs photodiode.

The first neural network has six neurons in the input layer L0 and two neurons in the output layer L3. As indicated above, the values of Hct % and Sat % at the output of the two calibration curves are two of the six input parameters of the neural network. As previously mentioned, the above first neural network (see also FIG. 12) may be sufficient to achieve the desired accuracy in the measurement of the parameters Sat % and Hct %; in such a case, the artificial intelligence of the device 1, 1' provides for a single neural network NN. However, if this is not sufficient and/or a higher accuracy is desired, the following second and third neural networks may also be used, or possibly a number of neural networks equal to two or a number of neural networks greater than three.

| 2$^{nd}$ Neural Network | Data matrix to determine neural network coefficients | Neural Network Output |
|---|---|---|
| Hct % dependence on Sat % It can be seen that this dependency can already be compensated for by the first neural network. In that case, the development of this second neural network would not be necessary. | Inputs: Sat % output from the calculation of the first neural network Hct % output from the calculation of the first neural network Target values to minimise error Sat % ABL reference instrument Hct % ABL reference instrument | Matrix of coefficients/ weights to compensate for dependencies of Hct % on Sat % |

The second neural network has two neurons in the input layer L0 (corresponding to the input values of Sat % and Hct % output from the calculation of the first neural network) and two neurons in the output layer L3 (corresponding to the output values of Sat % and Hct % detected).

| 3$^{rd}$ Neural Network | Data matrix to determine neural network coefficients | Neural Network Output |
|---|---|---|
| Dependence of Hct % on Blood Temperature It can be seen that this dependency can already be compensated for by the first neural network. In that case, the development of this third neural network would not be necessary; in such case, the first neural network is sufficient | Inputs: Sat % output from the calculation of the second neural network Hct % output from the calculation of the second neural network Tfluid (Blood temperature) Optical counts/ratios at different Sat % values (10-15 Sat % values at different Hct %), Hct % (15%, 20%, 30%, 40%, 50%) and fluid temperature (10° C., 15° C., 24° C., 32° C., 37° C. and 41° C.) Target values to minimise error Sat % ABL reference instrument Hct % ABL reference instrument | Matrix of coefficients/ weights to compensate for dependencies of Hct % on Tblood |

The third neural network has two neurons in the input layer L0 (corresponding to the input values of Sat % and Hct % output from the calculation of the second neural network and the blood temperature) and two neurons in the output layer L3 (corresponding to the output values of Sat % and Hct % detected).

When the neural networks have been developed/designed and the coefficients/weights of the calculation matrices have been identified, the inputs/outputs of the network are as follows.

| Neural Network | Input variables | Output variables |
|---|---|---|
| Calculation of Sat % and Hct % throughout the range | Sat % and Hct % measured by the probe from the two initial calibration curves Optical counts/ratios at different values of Sat % (10-15 values of Sat % at different Hct %) of Hct % (at Sat 20%, 30%, 40% and 50%) and fluid temperature (10° C., 15° C., 24° C., 32° C., 37° C. and 41° C.) Namely: Sat % Probe, Hct % Probe, Optical count ratio 805/660, Optical Count Ratio 805/1450, Optical count ratio 805/1550 (or alternatively optical count ratio 940/1050) Tfluid (blood temperature) | Sat % accurate Hct % accurate |
| Hct dependence on Sat (not required if first neural network does everything) | Sat % output from the calculation of the first neural network Hct % output from the calculation of the first neural network | Sat % accurate compensated for dependency Hct % Hct % accurate compensated for dependency Sat % |
| Hct dependence on temperature (not required if first neural network does everything) | Sat % output from the calculation of the second neural network. Hct % output from the calculation of the second neural network Fluid T (blood temperature) | Final Sat % Final Hct % |

Therefore, in the case of using a plurality of neural networks, the structure of the neural networks is the same, apart from the number of neurons of the input layer L0 and the corresponding input values, which vary according to the type of network to be designed. The output data, calculated by the neural network(s) by artificial intelligence are for each neural network the Sat % and Hct % values, while the Hb (hemoglobin) value is then calculated mathematically as it is derived from the hematocrit value. The Hb value can be calculated according to the following formula (relative to the reference blood analyser 69): Hb (g/dL)=Hct %/approx. 3.

Preparation (Calibration) of the Devices after Training

Every device 1, 1' produced after the training of devices 1L, 1L' described above is equipped with firmware that takes the above algorithm into account and is therefore equipped with artificial intelligence.

For each of these devices 1, 1', instead of having to perform the full training described above, only two curves are acquired, namely a fixed Sat % calibration curve and a fixed Hct % calibration curve. In the laboratory, it is therefore necessary to acquire these two curves so that the probe has all the necessary inputs to provide the required outputs. We can think of them as the curves that allow the probe to provide an initial saturation and hematocrit, which the probe will use as input along with the optical count ratios for each measurement (see FIG. 12, two neurons in the L0 input layer are dedicated to these two input values). The two calibration curves above are similar to those shown in FIG. 10 (hematocrit calibration curve) and FIG. 11 saturation calibration curve. Artificial intelligence allows the device 1, 1' to be calibrated from these two calibration curves; the device is then ready to be used to take measurements of the plurality of parameters.

In other words, each device 1, 1' that is produced after training the probes 1L, 1L' is calibrated in the laboratory (using the aforementioned calibration curves), so that the end user of the device 1, 1' does not have to perform a calibration, and consequently has an instrument immediately ready for use. This calibration in the laboratory is relatively quick (e.g. a few tens of minutes or a few hours); in essence, two calibration curves are acquired, preferably at a blood temperature of 37° C., as described above so that device 1, 1' has all the necessary inputs to output the required parameter values. In essence, this step of acquiring just two curves serves as the only calibration operation for each newly manufactured probe and allows for variability between probes (hardware, component variability and their geometric position, even infinitesimal in the probe housing) to be taken into account and to give a firm starting point for the Sat % and Hct % measurement expected under calibration conditions.

Identification of the Dependency on the Type (Colour/Shade) of the Tubes with which the Devices in Accordance with the Second Embodiment are Associated It is intended to exploit the LED elements of the 525 nm and 940 nm wavelengths to identify the type dependency of the tube with which the device 1' is associated. One acquires the optical counts for these wavelengths by having saline solution in the tubes 25' (i.e. before blood flows into the tubes) and then derives the factors (coefficients, i.e. weights and biases, of the neural network NN, which are as many as the number of neurons) to be used.

The different colour tones of the tubes have an impact on the optical counts detected at these wavelengths. Each tube 25' is identified on the basis of a mathematical relationship based on these two optical counts.

Identification of Dependency on the Blood Flow

In order to identify the dependence of saturation on blood flow, the variation of the optical counts of the 940 nm wavelength LED element as a function of flow is used. Blood flow is preferably the volumetric flow rate of blood flowing into the extracorporeal blood circuit and thus into the tube 25' and can be measured in litres/minute. Basically, as the optical counts of the 940 nm wavelength LED element are Sat % dependent, compensation for this dependence is required. The counts resulting from the excitation of the LED element at 940 nm are affected by both blood flow and saturation; in order to be able to use them for flow detection, it has to be ensured that they do not depend on saturation.

By introducing an additional excitation LED element of wavelength 1050 nm, which varies with Sat %, mounted on the same excitation member as the 940 nm LED element (first excitation member), then detected with the same photodiode (first photodetector), a 'second' saturation (ratio of counts against 940 nm excitation to counts against 1050 nm excitation) is then to be acquired to compensate for the variation of the 940 nm wavelength LED element and thus free it from saturation dependence for flux detection.

The flow information thus obtained is used to develop an algorithm for correcting Sat % and Hct % in dependence of blood flow.

Clinical Use of the Device

The invention further relates to a use of the previously described device 1, 1'. The use of the device 1, 1' is for measuring a plurality of blood parameters; the parameters are of the type described above.

The use does not require, and therefore does not include, an initial calibration of the device. The use is preferably a clinical use, in which the device 1, 1' may be used in cooperation with a medical machine 90', 90', such as the heart-lung machine 90' or the extracorporeal membrane oxygenation (ECMO) machine 90' or others. Due to the training, the device does not require any initial calibration and is therefore of the ready-to-use type.

FIGS. 8A and 8B illustrate respective apparatus 100 and possible clinical uses of the device 1, 1' in accordance with the invention. In more detail, FIG. 8A illustrates the clinical use of the device 1, 1' in an operating theater, wherein the device 1, 1' is used in cooperation with a heart-lung machine 90', to which it is connected. As for FIG. 8B, it illustrates the clinical use of the device in an intensive care unit, in which the device 1, 1' is used in cooperation with an extracorporeal membrane oxygenation machine 90', to which it is connected. An example of intensive care where it may be appropriate to use the device 1 according to the invention is intensive care due to Covid, where monitoring one or more parameters related to the presence or concentration of oxygen in the blood may be of vital importance.

The measured parameter values are made available to the medical personnel in charge, e.g. at a user interface of the medical machine 90', 90". Parameter values can be provided to the medical machine 90', 90" continuously or at a certain cadence and, additionally or alternatively, at the request of the medical machine 90', 90".

Clearly, the device 1 is suitable for additional clinical uses beyond those described here, particularly in combination with any additional medical machine and/or in any therapy or scope requiring extracorporeal blood circulation.

Apparatus

The invention further relates to an apparatus 100 comprising a device 1, 1' of the type described above and a medical machine 90', 90". The device 1, 1' is configured to cooperate and dialogue with the medical machine 90', 90".

The medical machine 90', 90" may be a heart-lung machine 90' or an extracorporeal membrane oxygenation machine 90' or other medical machine. The medical machine 90', 90" may include a user interface configured to make available parameter values measured by the device 1, 1'. The user interface may include a display means 91, 91', such as a screen 91, for displaying said values. The display means 91 is operatively connected or connectable to the device 1, 1'. The display means 91 may be part of, or associated or connectable to, the medical machine. In FIGS. 8A and 8B, both a device 1 in accordance with the first embodiment and a device 1' in accordance with the second embodiment are shown; in FIG. 8A, they are respectively connected to a screen 91 integrated in the medical machine 90', 90" and to a screen 91' capable of displaying physiological parameters, while in FIG. 8B, they are connected to a same screen 91 integrated in the medical machine 90', 90". Alternatively, the user interface may make parameter values available or communicate them to medical personnel in another manner.

The apparatus 100 comprises an extra-corporeal blood circuit 92 configured to circulate blood. The extra-corporeal blood circuit 92 connects the medical machine 90', 90" to the patient; a cuvette may be displaced along the circuit to which a device 1 is associated in accordance with the first embodiment. Each of FIGS. 8A, 8B further shows a device 1' in accordance with the second embodiment directly associated with the extra-corporeal blood circuit tube 92. In essence, the device 1, 1' may constitute an appendage of the medical machine 90', 90' which functionally acts as a sensor intended to measure a plurality of parameters of the blood circulating in the extra-corporeal blood circuit 92.

Method for Measuring a Plurality of Blood Parameters

The present invention also relates to a method for measuring a plurality of blood parameters, the parameters being of the type described above. The method is preferably carried out by means of the device 1, 1' described above.

The method comprises at least the following steps:
  exciting a blood flow with electromagnetic radiation at a plurality of determined wavelengths,
  detecting a plurality of electromagnetic responses, in particular light responses, of the blood comprising electromagnetic radiation, in particular light, retro-reflected or diffused by the blood, receiving analogue information about the plurality of electromagnetic and/or light responses of the blood including light retro-reflected or diffused by the blood, converting the electromagnetic and/or light response analog information into electro-magnetic and/or light response digital data, processing said electromagnetic and/or light response digital data and the actual temperature value of blood by one or more neural networks NN, determining, as a result of the processing operation by means of one or more neural networks NN, the value of each parameter of the plurality of blood parameters.

The latter two steps involve the following steps:

determining a plurality of ratios, each ratio being defined between a magnitude indicative of the radiation retro-reflected or diffused by the blood due to an excitation at a determined wavelength and a magnitude indicative of the radiation retro-reflected or diffused by the blood due to an excitation at another determined wavelength, providing input to one or more neural networks NN said plurality of ratios and the temperature value, processing said plurality of ratios by means of one or more neural networks NN taking into account a plurality of data of previous measurements of said blood parameters made during previous training, providing as an output from the one or more neural networks NN the value of each parameter of said plurality of blood parameters.

The method may provide for steps corresponding to one or more of the operations described above with reference to the control unit.

The method involves measuring the oxygen saturation, hematocrit and hemoglobin of the blood by means of artificial intelligence, of which the oxygen saturation, hematocrit directly by means of the artificial intelligence described above and hemoglobin indirectly, i.e. as a measurement derived from the hematocrit value.

The method further provides for measuring the actual temperature of the blood, preferably by means of the appropriate temperature sensor 12; this temperature constitutes both an input parameter for the one or more neural networks and an output parameter of the device, made available and viewable by the end user of the device on an appropriate display means.

The method may comprise the step of taking into account a value related to blood flow, in particular the volumetric flow rate of blood, when measuring oxygen saturation and/or hematocrit. This step may involve correcting the measured values of oxygen saturation and/or hematocrit depending on the blood flow.

Before exciting the blood flow with electromagnetic radiation at a plurality of determined wavelengths, the method comprises the step of coupling the device 1, 1' to a corresponding container 25, 25'.

Specific Method Steps for the First Embodiment of the Device

The step of coupling the device 1 to a cuvette 25 may be performed by coupling the one or more coupling elements 17e, 17f of the device 1 with the one or more corresponding coupling elements 25b, 25c of the cuvette 25.

Specific Method Steps for the Second Embodiment of the Device

The step of coupling the device 1' to a container 25' can be carried out by housing a portion of the tube 25' of an extracorporeal blood circuit at the seat 19 of the box body 2 of the device 1' and bringing the covering element 18, 18' into an operative configuration (closing the covering element 18, 18' on the box body 2). Said step includes moving the covering element 18, 18' approaching the constraining elements 22, 23 displaced on the box body until determining the engagement of the movable elements 22a, 23a with the respective seats defined on the opposing operative ends 21a, 21b of the closing portion 21 of the covering element 18, 18'.

Figure 6A:
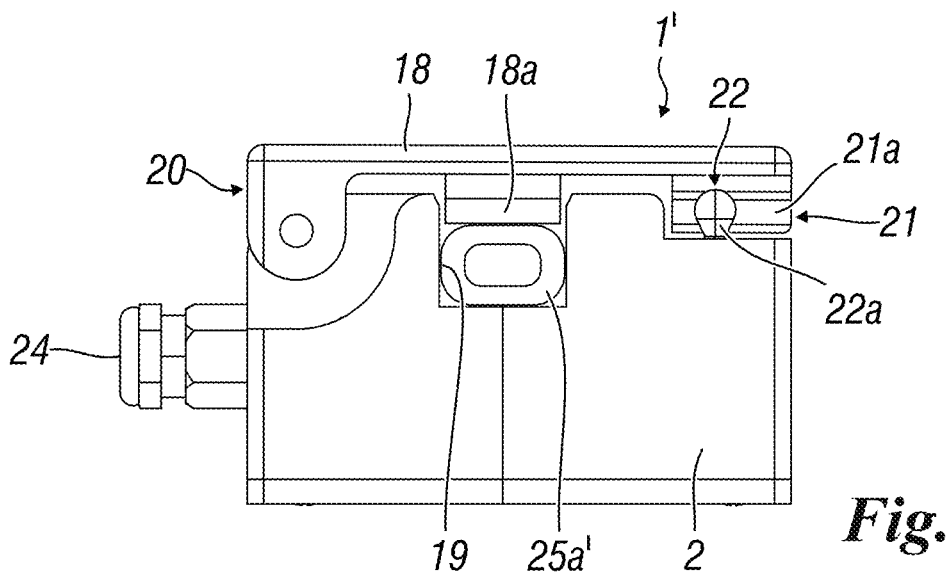
FIG. 6A illustrates a side view of the device of FIG. 6, showing how the covering element flattens the opposing surfaces of the tube housed in the seat; flattening is achieved by compressing the tube.

The closure of the covering element 18, 18' results in the compression of a central portion 25a' of the tube 25' within which blood flows and the flattening of opposing surfaces of the engaged portion of the tube 25' at the seat 19 by compression of these surfaces (see FIG. 6A). The compression step results in a reduction of the blood passage section of the tube 25' by between 9% and 17%, for a length of between 15 and 30 mm or equal to one of these values.

In the embodiment in which an oscillating compression element 180 is provided, the step of closing the covering element 18' comprises oscillating the compression element 180 with respect to the body 18b of the covering element 18' and thus with respect to the tube 15' within which blood flows. Such closing step comprises progressively and gently compressing the tube 25', thereby gently altering the flow of blood flowing within the tube 25'.

The method can enable the detection of a type of tube 25'. The step of detecting a tube type 25' is carried out prior to the step of exciting a flow of blood at a plurality of determined wavelengths. The method may prepare the control unit 3 of the device 1 for measurement based on the detected tube type 25'. The latter step may involve adapting the mode of measurement of one or more parameters to the type of tube 25' detected. Preferably, the step of detecting a tube type 25' comprises detecting the colour of the tube. The step of detecting a type of tube 25' is carried out while a saline solution or other fluid other than blood is flowing in the container. Preferably, the step of adapting the mode of measurement of one or more parameters to the type of tube 25' detected comprises selecting a determined matrix from a plurality of matrices usable by the neural network (each matrix may correspond to a particular colour or shade of tube). This selection can be made by consulting a memory (EEPROM memory) in which information relating to the plurality of matrices is stored.

Examples of Possible Modifications

The present invention may be subject to modification and/or further improvement.

For example, the device 1, 1', in particular the device 1' according to the second embodiment, may be provided with a display means, such as a display, on which blood parameters are shown. Such blood parameters may be initially calculated assuming that a standard tube (i.e. a tube of a most commonly used colour or shade) is coupled to the device 1'. The device 1' may provide that on the display means there is the possibility of entering as input the type of tube 25' actually coupled to the device 1' (in particular the type of tube 25' in terms of its colour or shade; for example, one might have to enter 1 for 'blue' tube, 2 for 'yellow' tube, etc.), so that the device 1' will automatically load the coefficient matrix of the associated neural network(s) and recalculate the blood parameters to take into account the tube actually coupled to the device 1'. The visualisation support and this interaction possibility makes the 'on-the-go' measurement option even more advantageous and faster.

The device 1' in accordance with the second embodiment may provide a sensor for verifying the position of the covering element 18, 18', in particular for verifying that the covering element 18, 18' is in the closed position (operating configuration). The control unit 3 may provide that the measurement of the parameters can only take place after verifying that the covering element 18, 18' is correctly in the closed position.

The control unit 3 described above provides a possible implementation of artificial intelligence according to the invention, which the Applicant has verified to be particularly efficient; however, possible modifications/improvements or further embodiments are not excluded. Similarly, different neural networks could be used to implement the artificial intelligence features of the present invention.

Further adjustments can be envisaged in the light of specific needs or contingencies relating to the implementation of the invention.

FURTHER ADVANTAGES AND CONCLUDING REMARKS

To summarise, the main advantages of the invention are as follows:
- the parameter measurements are taken without the user having to carry out any calibration of the device 1, 1'; in essence, in clinical use, the user has a device 1, 1' immediately ready for use as it has on board all the information needed to take measurements of the blood parameters of interest,
- the device 1, 1' is autonomous in terms of measurement, i.e. it does not depend on other instrumentation external to device 1, 1' itself to carry out the parameter measurement; external instrumentation may only be used to make the measured parameter values available,
- the measurements made by artificial intelligence are reliable over the entire measurement range of the parameters; in more detail, they show accuracy of +6% over the entire measurement range of the parameter Sat % and for all operating conditions and accuracy of +3% over the entire measurement range of the parameter Hct % and for all operating conditions,
- measurements are made by means of a compact, space-saving, lightweight device 1, 1' with appropriately miniaturised components.

The protection conferred by the claims extends to each element, component and/or step of the invention equivalent to the one(s) claimed. It is thus understood that each element, component and/or step of the product/method according to the invention may be substituted with an equivalent element, component and/or step (hereinafter, "equivalent(s)"); such equivalent(s) may already exist on the date of filing or priority of this patent text or subsequent conception/development.

The invention claimed is:

1. A device (1, 1') for measuring a plurality of blood parameters by artificial intelligence comprising:
at least one excitation member (4, 5) configured to excite blood, particularly a blood flow, by electromagnetic radiations at a plurality of determined wavelengths,
at least one electromagnetic radiation detecting member (8, 9), particularly at least one photodetector, configured to detect a plurality of electromagnetic responses, particularly light responses, of blood comprising electromagnetic radiations, particularly light, retroreflected or diffused by blood, the electromagnetic radiations being retroreflected or diffused by blood in operative conditions of the device (1, 1') upon an excitation by the excitation member (4, 5),
a control unit (3) configured to perform the following operations:
commanding said at least one excitation member (4, 5) during an excitation step wherein it excites blood by electromagnetic radiations at a plurality of determined wavelengths,
receiving analog information regarding a plurality of electromagnetic and/or light responses of blood comprising electromagnetic radiations, particularly light, retroreflected or diffused by blood,
converting the electromagnetic and/or light response analog information into electromagnetic and/or light response digital data,
processing said electromagnetic and/or light response digital data and the actual temperature value of blood by one or more neural networks (NN),
determining, as a result of the processing operation by the one or more neural networks (NN), the value of each parameter of said plurality of blood parameters,
the control unit (3) being configured to process said electromagnetic and/or light response digital data and the actual temperature value of blood by one or more neural networks (NN) and to determine the value of each parameter of said plurality of blood parameters by the following operations:
determining a plurality of ratios, each ratio being defined between a magnitude indicative of the radiation retroreflected or diffused by blood due to an excitation at a determined wavelength and a magnitude indicative of the radiation retroreflected or diffused by blood due to an excitation at another determined wavelength,
providing as an input to the one or more neural networks (NN) said plurality of ratios and the temperature value,
processing said plurality of ratios by the one or more neural networks (NN) by considering a plurality of data of previous measurements of said blood parameters performed during previous training,
providing as an output from the one or more neural networks (NN) the value of each parameter of said plurality of blood parameters,
wherein the device (1, 1') comprises also:
a box body (2), said at least one or each of the excitation member (4, 5), said at least one or each of the electromagnetic radiation detecting member (8, 9) and the control unit (3) being housed within the box body (2),
a coupling portion (17, 19) configured to allow coupling of the device (1, 1') to a container (25, 25') in which said blood can flow, the coupling portion (17, 19) being joined to the box body (2).

2. The device according to claim 1, wherein the control unit (3) is configured to detect the value of each parameter of said plurality of blood parameters which the artificial intelligence considers corresponding, based on said plurality of data of previous measurements, to the beforehand determined ratios.

3. The device according to claim 1, further comprising firmware and the control unit (3) comprises artificial intelligence information, comprising one or more matrixes useable by said one or more neural networks (NN), coded in the firmware and apt to enable calculating said plurality of blood parameters by one or more neural networks (NN).

4. The device according to claim 1, further comprising memory, and the control unit (3) being configured to provide as input to the one or more neural networks (NN) a reference value of a first parameter to be measured and a reference value of a second parameter to be measured, said reference values being acquired and stored in the memory of the device (1, 1') during a calibration step before using the device (1, 1'), said memory comprising information regarding said reference values.

5. The device according to claim 1, wherein the device (1, 1') is configured to measure, by means of artificial intelligence, the oxygen saturation (SatO2), hematocrit (Hct), and optionally the contents of hemoglobin (Hb).

6. The device according to claim 1, wherein the control unit (3) is configured to command said at least one excitation member (4, 5) or both the excitation members (4, 5) during an excitation step which excites blood flow at a wavelength at a time.

7. The device according to claim 1, wherein said at least one excitation member (4, 5) is configured to excite a blood flow at the following wavelengths: 660 nm, 805 nm, 1450 nm and at least one of the following wavelengths: 525 nm, 940 nm, and 1050 nm.

8. The device according to claim 1, comprising a first excitation member (4) configured to excite blood flow at least at a first plurality of wavelengths and a second excitation member (5) configured to excite blood flow at a second plurality of wavelengths; the control unit (3) being configured to alternately activate the first excitation member (4) and the second excitation member (5) in order to alternately excite blood flow at the first plurality of wavelengths and at the second plurality of wavelengths.

9. The device according to claim 1, wherein the device (1, 1') has a volume between 20,000 mm$^3$ and 400,000 mm$^3$.

10. The device according to claim 1, the device (1, 1') in combination with a container (25, 25'), in which blood can flow, wherein, in operative conditions, the device (1, 1') is associated to said container (25, 25') and the control unit (3) is configured to perform operations of: detecting a type of container (25, 25'); getting ready to measure, based on the detected type of container (25, 25').

11. The device according to claim 10, the device (1, 1')) in combination with a tube (25') and the control unit (3) is configured to detect the color of the tube (25') and to perform the operation to get ready to measure based on the color of the tube (25') detected by a selection of a determined matrix among a plurality of matrixes that are useable by the neural network (NN).

12. The device according to claim 1, comprising a covering element (18, 18') movable with respect to the box body (2) and a seat (19) apt to house a container (25, 25'), particularly a portion of a tube (25'), in which blood flows in operative conditions of the device (1'), the covering element (18, 18') being configured to operate at least between the following configurations: an operative configuration in which it flattens out the opposite surfaces of the container (25, 25') housed at the seat, a rest configuration.

13. The device according to claim 12, wherein the covering element (18, 18') comprises a compression element (18a, 18o) apt to compress, in the operative configuration of the covering element (18, 18'), the container (25') housed at the seat (19).

14. The device according to claim 13, wherein the compression element (18a, 18o) is configured to determine an amount of reduction of the fluid passage cross-section of the container (25') housed at the seat (19) comprised between 9% and 17%.

15. The device according to claim 13, wherein the covering element (18') comprises a body (18b) and the compression element (18o) is configured to oscillate with respect to said body (18b).

16. The device according to claim 1, further comprising a temperature sensor (12) housed inside the box body (2) of the device (1, 1') and configured to measure the actual temperature value of blood.

17. The device according to claim 1, wherein the coupling portion (17, 19) is integral with the box body (2).

18. An apparatus (100) comprising: a device (1, 1') according to claim 1,
a medical machine (90', 90"), a heart-lung machine (90') or an extracorporeal membrane oxygenation machine (90"),
a user interface, comprising a display means (91), operatively connected or connectable to the device (1, 1') and configured to provide the measured values of said plurality of blood parameters.

19. Method of measuring a plurality of blood parameters by artificial intelligence, the method comprising the following steps:
exciting blood, particularly a blood flow, by electromagnetic radiations at a plurality of determined wavelengths,
detecting a plurality of electromagnetic responses, particularly of light responses, of blood, comprising electromagnetic radiations, particularly light, retroreflected or diffused by blood,
receiving analog information regarding the plurality of electromagnetic and/or light responses of blood comprising light retroreflected or diffused by blood,
converting the electromagnetic and/or light response analog information into electromagnetic and/or light response digital data,
processing said electromagnetic and/or light response digital data and the actual temperature value of blood by one or more neural networks (NN),
determining, as a result of the processing operation by the one or more neural networks (NN), the value of each parameter of said plurality of blood parameters,
wherein the steps of processing said electromagnetic and/or light response digital data and the actual temperature value of blood by the one or more neural networks (NN) and determining the value of each parameter of said plurality of blood parameters comprise:
determining a plurality of ratios, each ratio being defined between a magnitude indicative of the radiation retroreflected or diffused by blood due to an excitation at a determined wavelength and a magnitude indicative of the radiation retroreflected or diffused by blood due to an excitation at another determined wavelength,
providing as an input to the one or more neural networks (NN) said plurality of ratios and the temperature value,
processing said plurality of ratios by the one or more neural networks (NN) by considering a plurality of data of previous measurements of said blood parameters performed during previous training,
providing as an output from the one or more neural networks (NN) the value of each parameter of said plurality of blood parameters.

20. Method according to claim 19, further comprising the step of compressing a portion (25a') of a container (25') in which blood flows or can flow, the step of compressing a portion (25a') of a container (25') comprising determining a reduction of the fluid passage cross-section of the container (25') comprised between 9% and 17%.

21. Method according to claim 19, further comprising the step of oscillating a compression element (18*o*) with respect to a container (25') in which blood flows or can flow.

22. Method according to claim 19 further comprising the steps of:
providing a device (1, 1') for measuring a plurality of blood parameters by artificial intelligence, the device comprising:
at least one excitation member (4, 5) configured to excite blood, particularly a blood flow, by electromagnetic radiations at a plurality of determined wavelengths,
at least one electromagnetic radiation detecting member (8, 9), particularly at least one photodetector, configured to detect a plurality of electromagnetic responses, particularly light responses, of blood comprising electromagnetic radiations, particularly light, retroreflected or diffused by blood, the electromagnetic radiations being retroreflected or diffused by blood in operative conditions of the device (1, 1') upon an excitation by the excitation member (4, 5),
a control unit (3) configured to perform the following operations:
commanding said at least one excitation member (4, 5) during an excitation step wherein it excites blood by electromagnetic radiations at a plurality of determined wavelengths,
receiving analog information regarding a plurality of electromagnetic and/or light responses of blood comprising electromagnetic radiations, particularly light, retroreflected or diffused by blood,
converting the electromagnetic and/or light response analog information into electromagnetic and/or light response digital data,
processing said electromagnetic and/or light response digital data and the actual temperature value of blood by one or more neural networks (NN),
determining, as a result of the processing operation by the one or more neural networks (NN), the value of each parameter of said plurality of blood parameters,
the control unit (3) being configured to process said electromagnetic and/or light response digital data and the actual temperature value of blood by one or more neural networks (NN) and to determine the value of each parameter of said plurality of blood parameters by the following operations:
determining a plurality of ratios, each ratio being defined between a magnitude indicative of the radiation retroreflected or diffused by blood due to an excitation at a determined wavelength and a magnitude indicative of the radiation retroreflected or diffused by blood due to an excitation at another determined wavelength,
providing as an input to the one or more neural networks (NN) said plurality of ratios and the temperature value,
processing said plurality of ratios by the one or more neural networks (NN) by considering a plurality of data of previous measurements of said blood parameters performed during previous training,
providing as an output from the one or more neural networks (NN) the value of each parameter of said plurality of blood parameters,
wherein the device (1, 1') comprises also:
a box body (2), said at least one or each of the excitation member (4, 5), said at least one or each of the electromagnetic radiation detecting member (8, 9) and the control unit (3) being housed within the box body (2),
a coupling portion (17, 19) configured to allow coupling of the device (1, 1') to a container (25, 25') in which said blood can flow, the coupling portion (17, 19) being joined to the box body (2), and
coupling the device (1, 1') to a container (25, 25') before the step of exciting blood, particularly the blood flow, by electromagnetic radiations at a plurality of determined wavelengths.

23. Method according to claim 19, comprising the step of detecting the actual temperature value of blood, preferably by means of a temperature sensor (12) housed inside the box body (2) of the device (1, 1').

\* \* \* \* \*